US012797243B2

(12) United States Patent
Horvath et al.

(10) Patent No.: US 12,797,243 B2
(45) Date of Patent: Nov. 17, 2026

(54) SYSTEMS AND METHODS FOR TREATING GLAUCOMA WITH PHOTODISRUPTIVE LASER PULSES

(71) Applicant: EYEX SOLUTIONS INC., San Juan Capistrano, CA (US)

(72) Inventors: Christopher Horvath, San Juan Capistrano, CA (US); Vanessa Isabella Vera, San Juan Capistrano, CA (US)

(73) Assignee: EyeX Solutions, Inc., San Juan Capistrano, CA (US)

( * ) Notice: Subject to any disclaimer, the term of this patent is extended or adjusted under 35 U.S.C. 154(b) by 171 days.

(21) Appl. No.: 16/740,456

(22) Filed: Jan. 12, 2020

(65) Prior Publication Data

US 2020/0146887 A1 May 14, 2020

Related U.S. Application Data

(60) Continuation of application No. 13/442,854, filed on Apr. 10, 2012, now Pat. No. 9,033,963, and a continuation of application No. 14/685,955, filed on Apr. 14, 2015, now Pat. No. 10,568,763, which is a division of application No. 13/442,854, filed on Apr. 10, 2012, now Pat. No. 9,033,963.

(60) Provisional application No. 61/473,806, filed on Apr. 10, 2011.

(51) Int. Cl.
*A61F 9/008* (2006.01)
*A61F 9/007* (2006.01)
*A61F 9/009* (2006.01)

(52) U.S. Cl.
CPC ...... *A61F 9/00821* (2013.01); *A61F 9/00781* (2013.01); *A61F 9/00825* (2013.01); *A61F 9/009* (2013.01); *A61F 2009/00868* (2013.01); *A61F 2009/00891* (2013.01)

(58) Field of Classification Search
CPC .............. A61F 9/00821; A61F 9/00814; A61F 9/00823; A61F 9/00825; A61F 9/00781; A61F 9/008; A61F 9/009; A61F 2009/00868; A61F 2009/00891; A61F 2009/00897
USPC .......................................................... 606/4–6
See application file for complete search history.

(56) References Cited

U.S. PATENT DOCUMENTS

| | | | | |
|---|---|---|---|---|
| 6,325,792 | B1 * | 12/2001 | Swinger | A61F 9/00804 606/11 |
| 9,237,967 | B2 * | 1/2016 | Gooding | A61B 90/39 |
| 10,335,315 | B2 * | 7/2019 | Goldshleger | A61F 9/009 |

* cited by examiner

*Primary Examiner* — Aaron F Roane
(74) *Attorney, Agent, or Firm* — Morgan, Lewis & Bockius LLP

(57) ABSTRACT

The invention relates to systems and methods for delivering highly focused photodisruptive laser pulses with pulse durations <50 picoseconds into the anterior chamber angle region of an eye, creating channels into various anatomical structures within the anterior angle of the eye and thereby facilitating aqueous outflow for the treatment of Glaucoma. The invention includes novel gonioscopy lens systems, patient interface systems and laser delivery systems to deliver such focused laser beams to the anterior angle area and other areas of the eye.

20 Claims, 47 Drawing Sheets

SYSTEMS AND METHODS FOR TREATING GLAUCOMA WITH PHOTODISRUPTIVE LASER PULSES

CROSS-REFERENCE TO RELATED APPLICATIONS

This is a continuation of application U.S. Ser. No. 13/442,854, now U.S. Pat. No. 9,033,963 B2 filed on Apr. 10, 2012 and is also related to the Divisional application U.S. Ser. No. 14/685,955. This application further claims the benefit of the U.S. provisional application No. 61/473,806, filed Apr. 10, 2011, the content of which is considered incorporated by reference herein in its entirety. To the extent the following description is inconsistent with the disclosure of the provisional application, the following description controls.

BACKGROUND OF THE INVENTION

Lasers have been used for several decades in the treatment of glaucoma. The 2 most common laser treatments for primary open angle glaucoma (POAG) are ALT (Argon Laser Trabeculoplasty) and SLT (Selective Laser Trabeculoplasty). See for example U.S. Pat. Nos. 3,884,236; 8,066,696; 5,549,596; 6,319,274. They work by applying laser pulses into the Trabecular Meshwork (in the anterior angle of the eye). These laser pulses are focused to around 50 micrometer diameter for ALT and around 400 micrometer for SLT. Those laser spots are targeted to lay over Schlemm's canal and cause an increased outflow through the treated Trabecular meshwork area. In both procedures at least 180 degrees of the eye angle is treated with typically 50 to 100 laser pulses (each pulse is applied to a new target zone-treatment area). The working mechanism for ALT is blanching of the Trabecular meshwork that increases the outflow by stretching the Trabecular Meshwork between the blanched (laser treated areas). The ALT laser with a typical setting of 600 mW and 0.1 s pulse duration (at 514 nm or 532 nm) causes a thermal tissue interaction. In SLT treatment the laser causes cavitation bubbles in the target tissue due to its shorter pulse duration of about 3 nanoseconds and higher peak power (created by pulse energies of around 0.3 mJ to 1.6 mJ).

Both procedures have a good success rate by increasing aqueous humor outflow that creates a substantial drop in intraocular pressure of around 20%. Both procedures can be performed in minutes with a simple slit lamp procedure in the office (no OR visit required). In both procedures, the eye does not need to be opened (non-invasive procedure), therefore the treatment risks and complication rates are minimal. The problem of these procedures as published in many studies is that it does not work effectively in all patients and in the successful cases the effect wears off over the course of a few (1-3 years) and the IOP rises back to its baseline level. The procedure can be repeated once with ALT and 2-3 times with SLT, but after those repeats the tissue damage in the Trabecular meshwork that is created through those multiple procedures ultimately prevents any further IOP lowering effect.

A less frequently used laser procedure called ELT (Excimer Laser Trabeculostomy) uses an Excimer laser pulse (wavelength in the UV range) to actually drill holes into the Trabecular Meshwork. See for example U.S patent applications: 20080082078; 20040082939. Because complete openings are created to Schlemm's canal (unlike ALT and SLT), the IOP lowering effect is similar or better than ALT/SLT and in the same time only a few open holes need to be drilled with ELT versus 50-100 treatment zones in a typical ALT/SLT procedure. Some studies further suggest that the ELT effect is longer lasting then ALT/SLT due to some observed long term patency of those holes. Furthermore ELT might be repeated more often since a smaller area of the Trabecular Meshwork is treated each time. The downside of ELT is the fact that UV wavelength light does not penetrate the cornea and aqueous humor, therefore the laser can only be applied to the Trabecular Meshwork in an operating room procedure, where the eye is opened and a fiber probe is inserted into the anterior chamber all the way up to the Trabecular Meshwork.

In recent years the effectiveness of having one or multiple holes in the Trabecular Meshwork (connecting to Schlemm's canal) has also been demonstrated with several implants, placed through the Trabecular Meshwork that create an opening into Schlemm's canal. See for example U.S patent applications: 20120071809, 20070276316. Those are however also invasive (full operating room) procedures using an implant.

Another approach to drain aqueous humor out of the anterior chamber has been successfully demonstrated by implanting a drainage tube through the scleral spur region and into the suprachoroidal space. See for example U.S patent application: 20110098629. This is however also an invasive (full operating room) procedures using an implant.

Most recently, there have been animal tissue studies applying ultrashort photodisruptive laser pulses to the trabecular meshwork with limited success. Hiroshi Nakamura et. al. Investigative Ophthalmology & Visual Science, March 2009, Vol. 50, No. 3. Performed an ex vivo study on primates delivering photodisruptive laser pulses into the anterior angle of the eye. He presents several limitations and challenges in the paper concerning the goal of creating a hole through the Trabecular Meshwork. These limitations and challenges have so far prevented a successful use of such a non-invasive laser procedure in the angle of the eye.

The inventions described herein relate to a new devices and methods to overcome those limitations and challenges and therefore allow the creation of holes and channels in the Trabecular Meshwork and other places in the angle of the eye in a non-invasive procedure that can be repeated as many times as necessary.

Other examples of related prior art are U.S. Pat. Nos. 8,056,564; 4,391,275; 5,288,288; 7,912,100

BRIEF SUMMARY OF THE INVENTION

Photodisruptive laser pulses in the range of <1000 femtoseconds have been successfully applied to make incisions into various tissues of the eye. The main focus to date has been using a femto second laser for various cornea incisions such as LASIK flaps, intrastromal incisions, Limbal Relaxing Incisions, Keratoplasties and cornea entry incisions. In more recent years femtosecond lasers have also been successfully applied to the capsule and the lens of the human eye in femtosecond laser assisted cataract procedures.

The main benefit of these photodisruptive laser pulses lays in the fact that the eye tissues, that are treated transmit the wavelengths of the typically chosen lasers, usually in the near infrared or visible range and therefore allow the laser to be focused through the cornea, aqueous humor, lens capsule and lens without much scattering or absorption. The laser pulses are always focused to a very small spot size in the range of a few micrometers, where a laser induced optical breakdown is achieved in any tissue or liquid (e.g. aqueous humor) that falls within the spot size location.

This optical breakdown (photodisruptive breakdown) creates a micro plasma followed by a small cavitation bubble, which can be used to cut and dissect tissue areas of any size and shapes by scanning a sequence of many such laser pulses over a desired volume in the eye.

Since the tissue layers in the laser path above and below the focus point are below the optical breakdown threshold and since they mostly the laser wavelength, they remain unaffected by the laser beam. This principle allows non-invasive photo disruptive eye surgery since no incision from the outside needs to be made.

There is a threshold of a minimum laser fluence (laser peak power divided by focus area) required to achieve the optical breakdown. The laser peak power goes up with higher pulse energy (typically in the ρJ range) and shorter pulse duration (typically <600 fs). The laser fluence for any given peak power goes up as the focus area goes down. Achieving a small spot size is therefore critical in achieving a high fluence that exceeds the optical breakdown threshold.

The way of achieving a high enough fluence for breakdown by increasing the laser pulse energy is less desirable since a higher pulse energy comes with a larger cavitation bubble and associated shock wave. The larger the cavitation bubble the less precision is achieved in cutting any features with a sequence of pulses. Furthermore a large shock wave is considered a undesired side effect since it has the potential to damage surrounding tissues.

Priority is therefore given to minimizing the spot size to achieve an above threshold laser fluence while using laser pulses within a low pulse energy range of <50ρJ per laser pulse.

These principles have been successfully implemented in femto second eye laser systems treating the cornea or capsule/lens of an eye. The laser delivery systems can achieve good focusing access to the cornea and lens through large focusing lens assemblies positioned within a few cm above the eye. Typical laser beam focusing convergence angles achieved are numerical apertures of NA>0.15 (full angle θ>15 deg) and in some optimized cases NA>0.3.

According to:

$$\Theta = M^2 \frac{360\ \lambda}{\pi^2\ \omega_0} \qquad \text{Formula 1}$$

Θ=full focusing convergence angle in degrees

λ=laser wavelength $\omega_0$=laser beam focus radius defined by $1/e^2$ cut off $M^2$=beam quality factor determined by the total aberrations If beam aberrations can be kept to a minimum e.g. $M^2<1.3$ ($M^2=1$ is the theoretical minimum with no aberration at all) then the above focusing angles of NA>0.15 (θ>15 deg) and NA>0.30 (θ>30 deg) the resulting spot size diameters ($2\ \omega_0$) will be <8 μm and <4 μm respectively (for a laser wavelength λ=1 μm).

The minimization of aberrations is critical in achieving such small spot sizes.

The tissue layers in the cornea and lens/capsule are relatively easy accessible for any laser beam from the outside.

Due to the fact that the existing systems focused laser beams enter the eye in a straight vertical line that is perpendicular to the central area of the cornea (and top surface of any used patient interface) the aberrations can be kept small enough to allow small spot sizes. Such femto-second cornea and lens/capsule systems typically reach beam quality factors of $M^2<2$.

The same easy access is not available for reaching the anterior camber angle tissue layers of the eye with a highly focused laser beam.

Furthermore the tissue layers in the anterior angle of the eye contain blood vessels that will start bleeding when hit or cut by photo disruptive laser pulses.

Therefore, there are several limitations and considerations that need to be overcome in order to deliver photo disruptive laser pulses to the anterior angle of the eye. Very limited success has been demonstrated so far in reaching these tissue layers (e.g. Trabecular Meshwork or scleral spur) with the goal of applying a laser pulse sequence that can create a drainage channel (hole) into and through those tissue layers.

Accessibility consideration factors for a highly convergent focused laser beam targeting the tissue layers of the anterior chamber angle:

Eye Anatomy:

The eye anatomy see FIG. 9 restricts the angular accessibility of the anterior angle (e.g. Trabecular Meshwork 3104) particularly in the vertical plane (defined here as a plane that includes the z-axis going centrally).

FIG. 3 shows a histology picture of the anterior angle in such a vertical cut. This eye shows a rather narrow angle of only 20 degrees. Typical angles in human eyes (including Primary Open Angle Glaucoma—POAG) are between 30 and 50 Degrees.

This vertical plane (vertical angle axis) represents the most restricted axis in terms of angular accessibility since the tangential access plane (the plane that includes the rim of the Trabecular Meshwork—perpendicular to the vertical plane) has a somewhat larger accessibility angle.

There are further factors limiting angular access to the eye (particular the already critical vertical plane).

Eye Geometry Variations:

The anterior angle accessibility varies widely from eye to eye. For example in highly myopic eyes the angle can be larger than 45 Degrees, while it becomes more narrow in Hyperopic eyes. FIG. 4 shows a more average 40 degree angle opening 3015.

Other Factors and Limitations of Anterior Angle Angular Access:

Total Internal Reflection, Gonioscopy Lens Requirement:

Due to the geometry of the cornea and anterior angle the light rays out of the anterior angle cannot exit the cornea due to total internal reflection. An optical interface with a similar index of refraction is therefore required on top of the cornea. This is called a gonioscopy lens (from here on referred to as a gonio lens). This invention includes several new gonio lens variations and designs that address and solve besides other features the wide angle laser delivery issues and limitations. FIG. 5 and FIG. 6 illustrate these principals.

Beam Aberrations:

The focusing laser beam has to go through several interfaces such as gonio lens, goniogel, cornea and aqueous humor. There are numerous cases of beam aberrations limiting the focusing power due to:

The wavefront of the beam hits many of those interfaces at high angles which is prone to cause astigmatism and higher order aberrations.

The interfaces curvatures such as the cornea vary from eye to eye and are not aberration free, especially at shallow incidence angles. The most upper vertical beam limit line runs at some point almost parallel to the cornea and endothelial cell layer. This causes significant aberrations in that part of the focusing laser beam. See for example FIG. 10.

The sagittal and tangential (vertical and horizontal) planes are exposed to significant different aberrations due to different interface curvatures in their respective planes.

The sagittal and tangential planes have different focusing requirements as discussed above (see FIG. 7) and therefore also experience different levels of aberrations.

All these factors need to be considered in the design and the methods of a delivery system, that can meet the small focusing requirements at the anterior angle. This invention addresses those limitations.

The limitations that need to be addressed and overcome can be summarized into the following categories:

The anatomical limitations of the human eye, in particular the relatively narrow access angle to the Trabecular Meshwork between the iris and the cornea are limiting the maximal possible focusing angle in that dimension. Furthermore human eyes show a great range of variability in this anatomical angle. In particular the last 1-2 mm before the actual chamber angle has great access variability between 0 deg (in case of a closed angle) to 50 deg opening based on the exact iris position.

Often the last 1 mm distance approaching the anterior angle from the center of the anterior chamber is hard to visualize even with a gonio lens a and can close off very rapidly due to iris synechia and iris bulging.

The laser beam cannot enter the eye perpendicular, but rather enters the cornea under a shallow and at some outer beam limits at an almost parallel angle. This dramatically increases the amount of aberrations that the laser beam wave front experiences during the beam propagation into the eye. Furthermore any contact interface and gonio lens that applies pressure to the cornea will induced aberrations such as cornea wrinkles that need to be overcome and/or compensated for.

The target region contains tissues of varying absorption and optical breakdown threshold characteristics since there is a great patient variability in pigmentation and presence of blood vessels or blood itself. These variations create large variability in the photo disruptive breakdown threshold fluency of the laser-tissue interactions and need to be considered and compensated for.

Due to total internal reflection, the angle is not directly accessible without the use of a gonio lens. A specific gonio lens design is required to minimize aberrations, allow for sufficient eye fixation and most importantly to allow transmission of a highly convergent laser beam as described above.

To allow integration of a gonio lens into a laser delivery system a patient interface with specific features is required.

The present inventions provide methods and systems for overcoming the limitations described above. In particular the invention provides the following methods and systems:

A first method to optimize the fs-laser beam parameters to reach, target and create holes into the tissue layers of the anterior angle of the eye: This will address the highly variable (eye to eye and setup to setup related) beam aberration variations and geometrical angle size variations of the anterior angle from eye to eye. Method to maximize the vertical angular laser beam access (and therefore achieving minimal spot size) at the anterior angle of an eye.

A second method to measure and maximize the vertical angular laser beam access and therefore achieving minimal spot size at the anterior angle tissue layers of an eye. The horizontal convergence angle of the treatment laser beam is fixed to preferably 60 deg (+/−20 deg) to create a small spot size in the horizontal axis in the range of <10 μm diameter depending on the overall aberrations.

A third method for delivering a particular pulse sequence of circular or elliptical spot size femtosecond laser pulses to create a hole(s) or channel(s) into the tissue layers of the anterior angle of an eye. The method describes a scanning pattern that can for example be applied during the laser firing in the first method step e. or the second method step f. to create the hole and channel into the desired target tissue layers. Method to target the treatment zone(s) using one or multiple lasers.

A forth method describing a laser scanning pattern to create a channel into the desired tissue layers of the anterior angle of the eye using a low cost minimal complexity laser delivery system.

A fifth method to automatically select and target multiple treatment zone(s).

A first system being a specific contact interface designs that includes gonio lens functionality and minimize beam aberrations to effectively deliver the highly converging laser beam into the anterior angle of the eye.

A second system being a specific patient interface designs that connect the laser delivery system to the specific contact interfaces.

Several other systems including patient interface designs and delivery system designs.

DETAILED DESCRIPTION OF THE INVENTION

Figure 9:
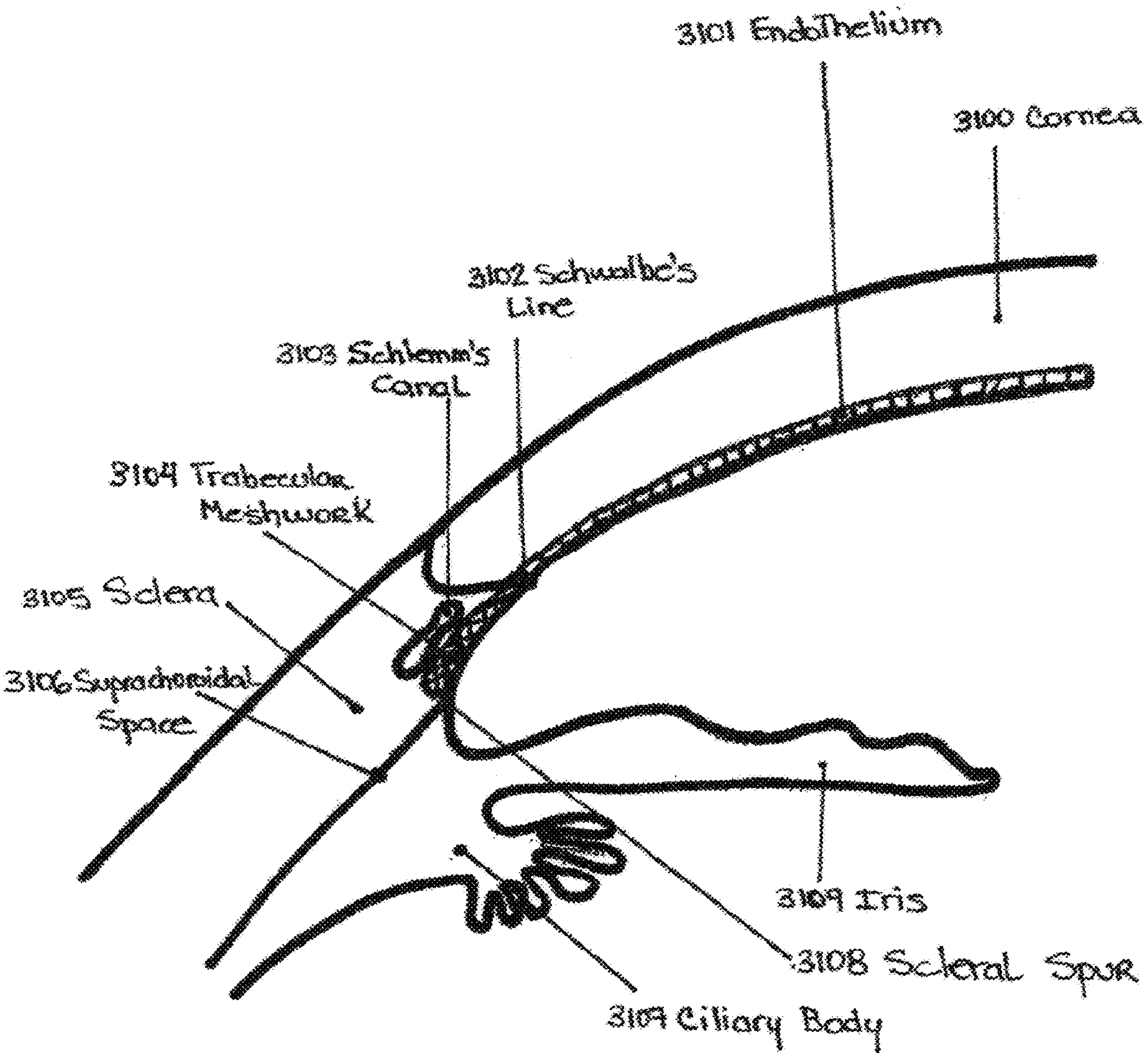
FIG. 9 shows the anatomical features of the anterior angle of an eye

The word "fs-laser" throughout this disclosure stands for femtosecond laser and is meant to cover any laser source, that can provide pulse durations smaller than <50000 femtoseconds (50 pico seconds) with a preferable range of 10 fs to 500 fs. The word femtosecond can also be interchanged with the word photodisruptive throughout the entire disclosure. This ultra-short pulse requirement together with a small spot size area (preferably <20 μm for circular focus and preferably <400 $\mu m^2$ for elliptical focus) allows the use of very small pulse energies in the range of <200 micro Joules (preferable range <50 micro joules) while still achieving a photodisruptive (plasma induced optical breakdown) tissue reaction that allows for the creation of a hole (tunnel) in tissue layers in the anterior angle of the eye (e.g the Trabecular Meshwork). FIG. 9 shows the anatomical features of the anterior angle area of the eye. It is critical to keep the pulse energies small since the undesired side effects such as shockwaves and large cavitation bubbles scale with the pulse energy, reduce precision and cause increasing collateral tissue damage around the desired target zone.

Figure 1:
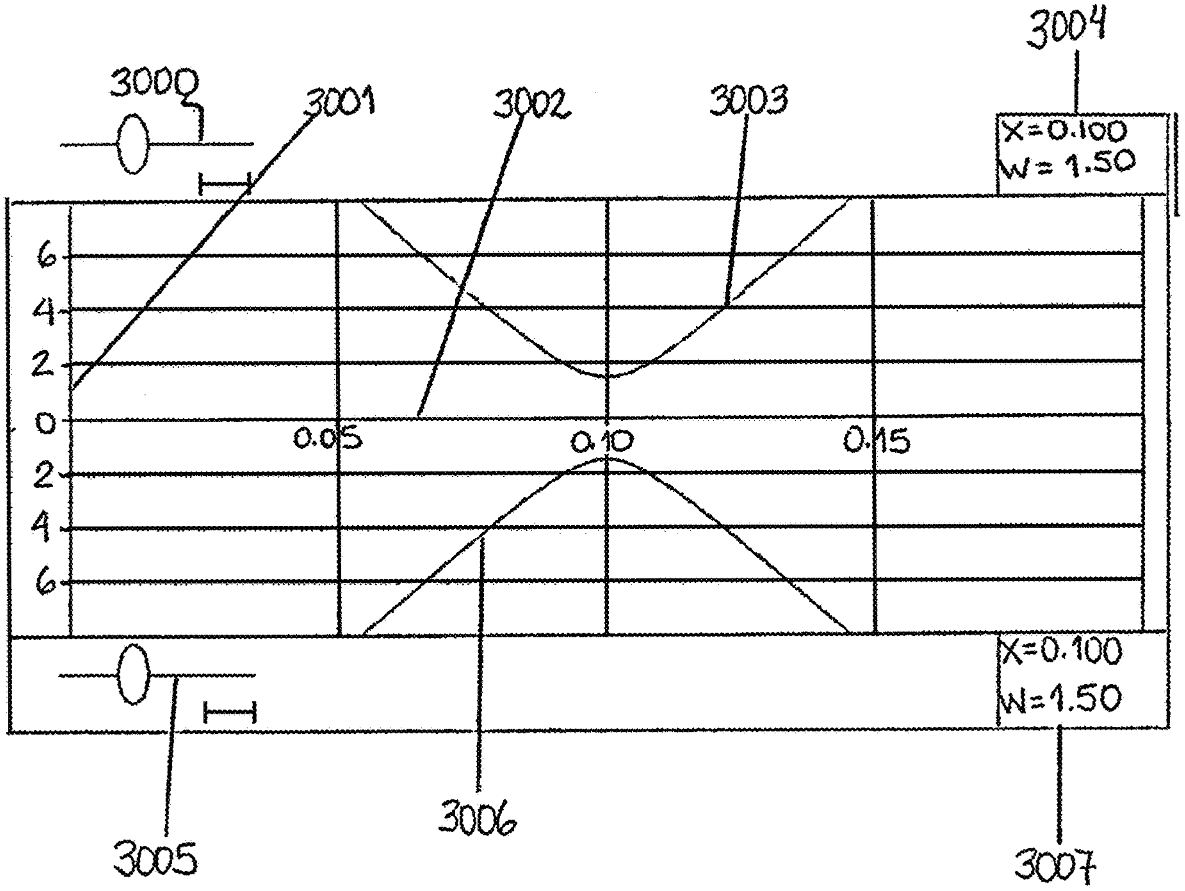
FIG. 1 illustrates a laser focus with a 3 μm diameter and a 20 deg convergence angle

FIG. 1. The small focus requirement leads to a large focusing beam convergence angle (high numerical aperture NA) in the range of 10-90 degrees. A 3 μm spot size diameter of a λ=1060 nm fs-laser beam with an aberration free beam quality factor of $M^2$=1 requires about 20 degrees (1/e^2) of full convergence (often referred to as beam divergence) angle as can be seen in the simulated coherent laser beam 3003 horizontal and 3006 vertical propagation calculation of FIG. 1.

Figure 2:
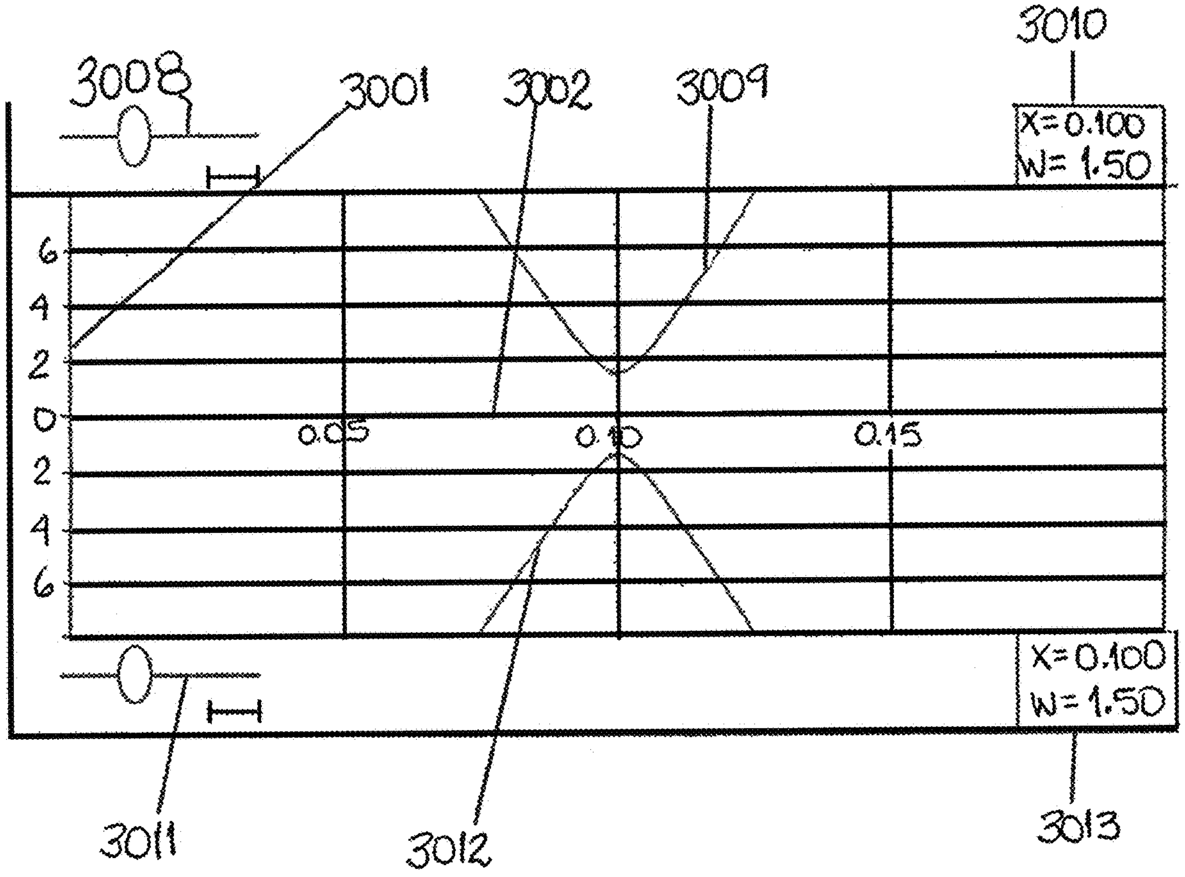
FIG. 2 illustrates a laser focus with a 3 μm diameter and a 40 deg convergence angle
Figure 3:
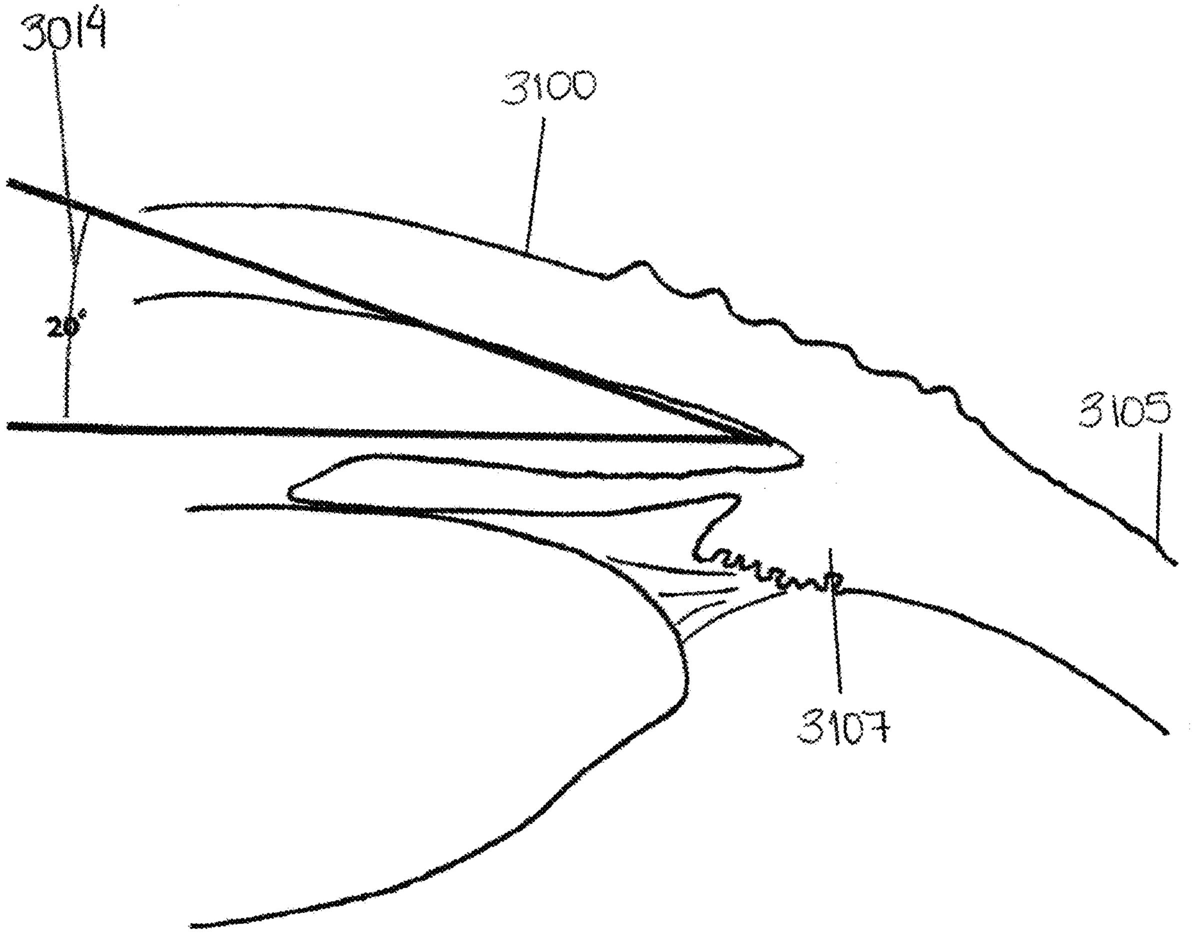
FIG. 3 illustrates a 20 deg laser focus into the anterior angle region of an eye
Figure 4:
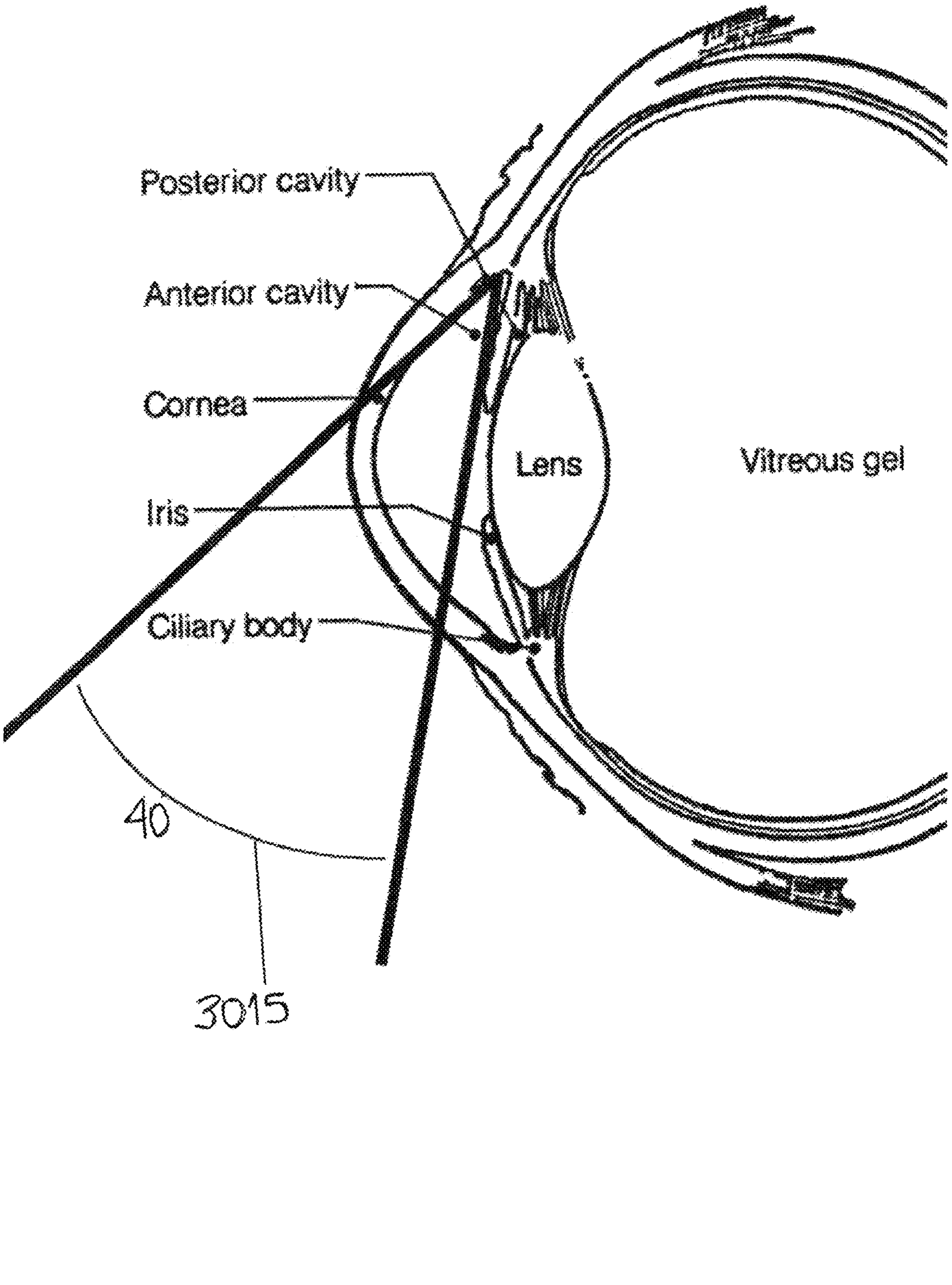
FIG. 4 illustrates a 40 deg laser focus into the anterior angle region of an eye
Figure 5:
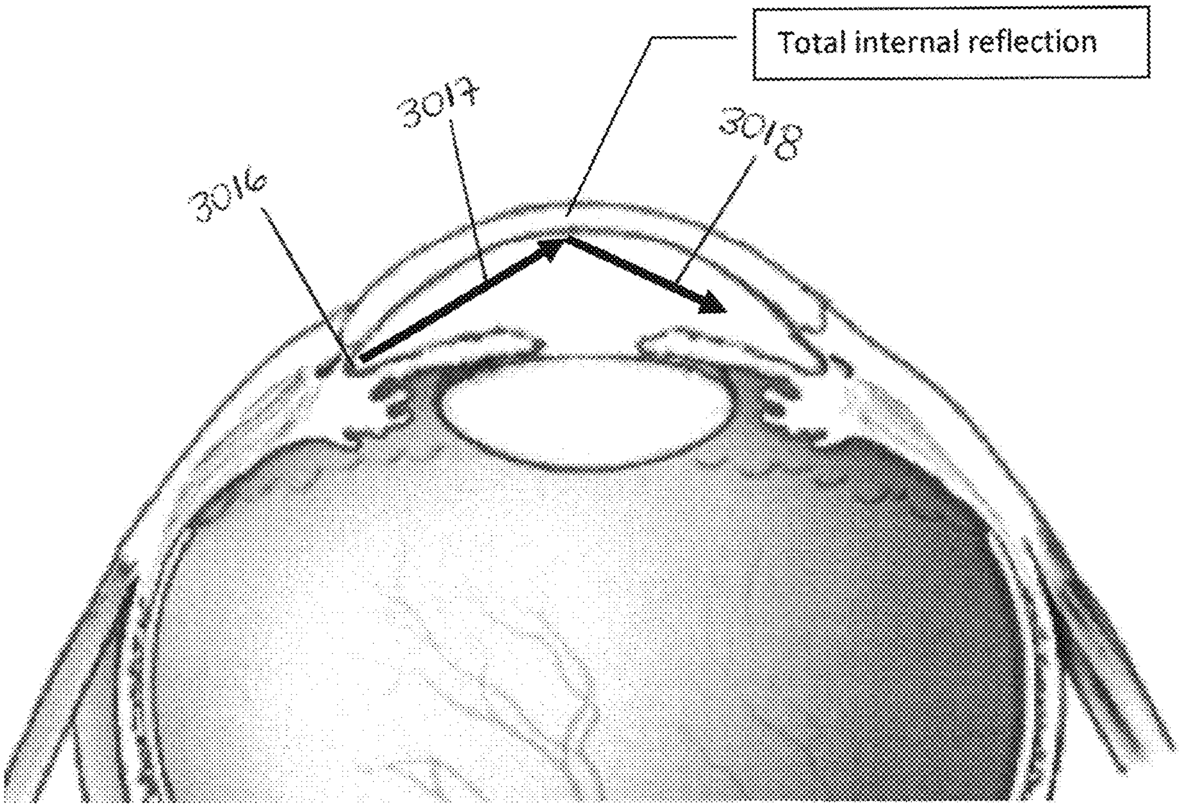
FIG. 5 shows the concept of total internal reflection

Because of significant wave front distortions of the laser beam, as it propagates through various optical and eye anatomical interfaces the coherence quality of the wave front is reduced resulting in a larger spot size. To maintain the same small spot size in the example above the full convergence angle to reach a 3 μm spot size diameter goes up to about 36 degrees (for an M^2 of 1.8) as shown in the simulation in FIG. 2.

Furthermore these theoretical values are defined as a 1/e^2 beam cut off value. If the beam had only exactly that room to propagate and anything outside this envelope would be cut off, then that would result in a larger focus and lost pulse energy due to clipping.

To prevent this additional aberration and energy loss it is important to allow another 5-10 degrees of accessible angle to prevent excessive clipping and to allow for some misalignment margin.

The present inventions provide systems and methods for overcoming the limitations described above. In particular the invention provides the following methods and systems:

A first method to optimize the fs-laser beam parameters to reach, target and create holes into the tissue layers of the anterior angle of the eye: This will address the highly variable (eye to eye and setup to setup related) beam aberration variations and geometrical angle size variations of the anterior angle from eye to eye. This method is described in the following steps from a. to f.

a. (Optional) When a laser delivery system with an adjustable beam convergency angle is used, pre-measured patient data of the anterior angle access angle e.g. through OCT (optical coherence tomography) before treatment is used to course adjust the vertical beam axis convergence angle (and horizontal axis in same way for circular focus version) to roughly match the accessible angle.

b. Use a delivery system with a fixed beam full convergence angle of 30 to 60 deg if circular or 30-60 deg in the vertical axis and 40-90 degrees in the horizontal axis if elliptical. The preferred full convergence angles are 40 deg (+/−5 deg) in both axis if a circular beam is delivered and 40 deg (+/−5 deg) in the vertical axis and 70 deg (+/−10 deg) in the horizontal axis if a delivery system is used that allows elliptical focusing. For most eyes with open angles these preferred settings will achieve a spot size at the anterior angle tissue layers that is close to a practical minimum. For eyes with partially closed angles <45 deg in the vertical access angle, the preferred settings will overfill the accessibility angle and this will result in some partial laser beam clipping in the vertical axis. The laser focus is then targeted into the desired tissue layer surface in the anterior angle of the eye and once the laser focus targeting has been completed the laser starts firing at a low pulse energy preferably <10ρJ. These probing laser pulses below the plasma breakdown threshold are then successively increased in pulse energy until first optical breakdown cavitation bubbles are detected (preferably by a vision system).

Figure 8:
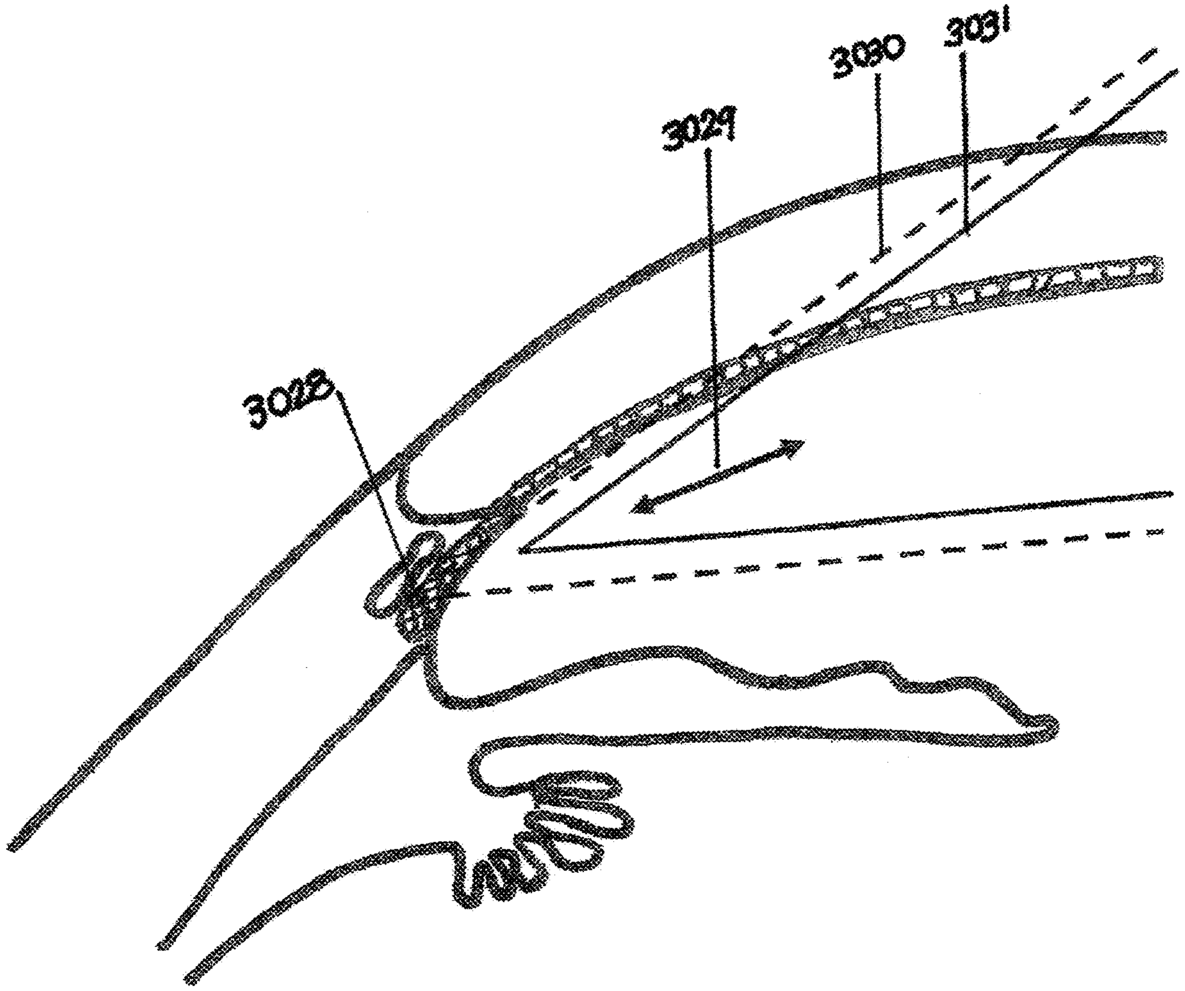
FIG. 8 illustrates a laser focus being scanned back and forward across a tissue interface
Figure 10:
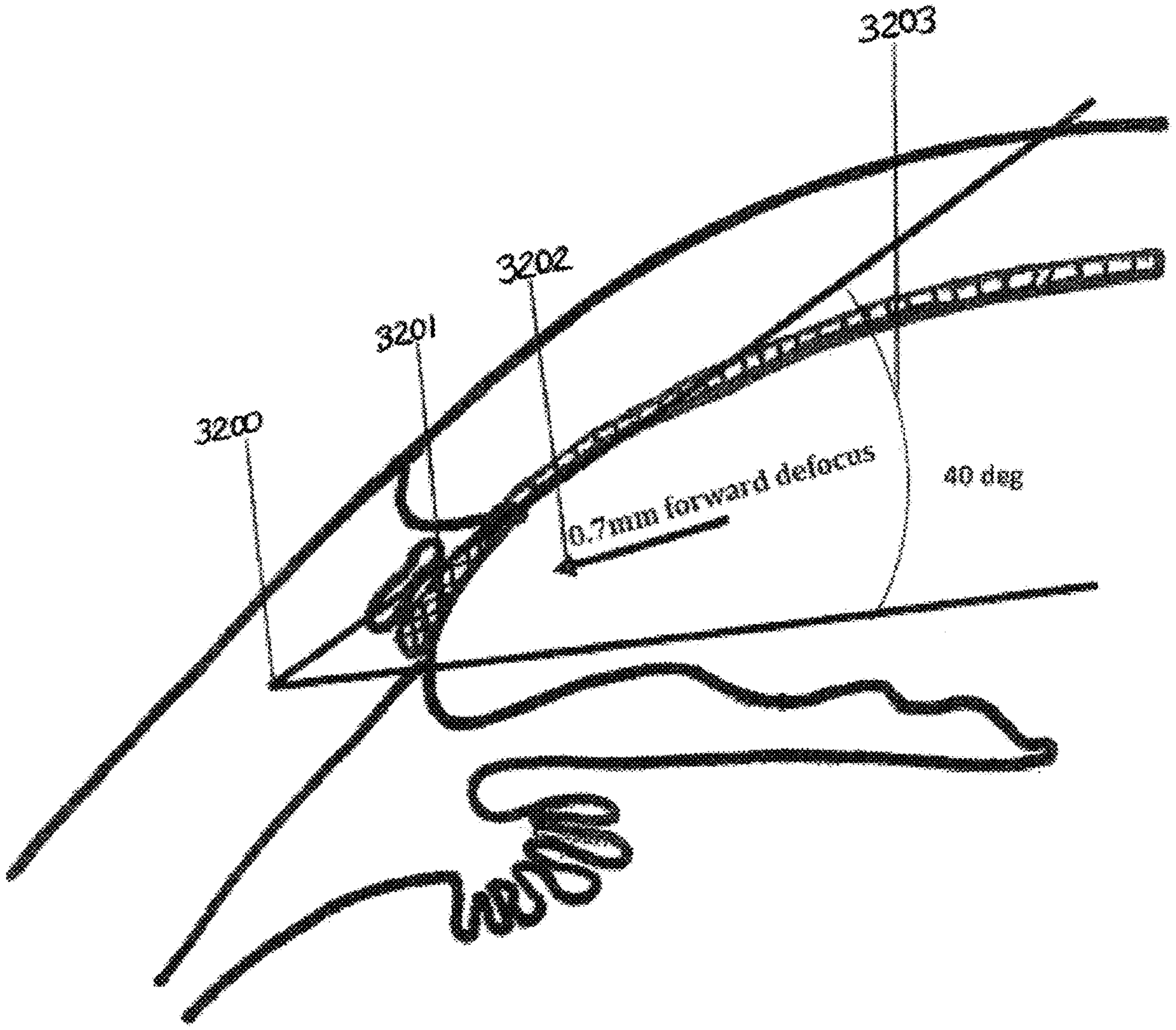
FIG. 10 illustrates a large photocoagulation zone due to a defocused laser beam

Step b-1. In one embodiment, an elliptical focus is delivered, e.g., vertical 10 μm×horizontal 3 μm, to make it much easier to deliver on the vertical angle. The laser pulse energy and scanning pattern are adjusted accordingly to optimize the hole drilling process.

c. (optional) see FIG. 8. The focusing lens and therefore the laser focus is scanned back 3031 and forward 3030 (preferably +/−<750 μm in z-axis 3029 while pulse energy is being increased in the sequence under b. to: assure the detected threshold happened on the surface of the targeted anterior angle tissue (e.g. Trabecular Meshwork) or closely below and not in the aqueous humor and to: calibrate the actual z-distance of a laser delivery system reference point (e.g. upper patient interface plane) to the surface of the targeted tissue layer in the anterior angle (e.g. trabecular meshwork surface).

d. (optional) Once the threshold has been determined as described in step b. (and optional the z-calibration in step c.) the same laser beam is preferably automatically defocused by a predetermined amount using a z-scan of the focusing lens or other lens in the delivery system. The preferred defocusing adjustment moves the laser focus 0.7 mm (+−0.5 mm) deeper into the target tissue (towards or into the sclera). This results in an enlargement of the laser beam diameter on the target tissue (surface of the anterior angle tissue layer) to about 500 μm FIG. 10, 3201 for a laser beam with a circular convergence angle of 40 deg 3203. After this defocusing adjustment 3202, resulting in a focus position in 3200, the pulse energy is automatically adjusted higher. This pulse energy is adjusted to a level such that the resulting average laser power $P_{average\ power}=E_{laser\ pulse\ energy}R_{laser\ repetition\ rate}$ times the applied laser on duration time during this defocused sequence provides an amount of total energy $E_{total}=P_{average\ power}\ t_{laser\ on\ duration}$ that photo coagulates the tissue area within the defocused diameter. For a preferred laser repetition rate >100 kHz and a preferred circular area of a 500 μm diameter beam and a preferred laser on duration of <1 s the preferred laser pulse energy is >10ρJ. Lower available pulse energy can be compensated by increasing the laser on duration to achieve the desired amount of photocoagulation. The laser beam area for this defocused large beam (e.g. 500 μm circular diameter) is typically >1000 times larger than typical achieved laser focus on the same surface without defocusing (e.g. 10 μm circular diameter). Therefore any conceivable rise in pulse energy (even to e.g. as high as >500ρJ) would still be far below the plasma threshold energy on this large area. Furthermore the new laser focus 0.7 mm below the anterior angle tissue layer surface is, because of significant photon scattering and absorption of the tissue layers between the surface layer and the 0.7 mm deep layer no longer reaching the fluency level required to exceed the plasma breakdown threshold. All laser power is therefore now absorbed and scattered creating a thermal effect in and around the defocused beam zone leading to photocoagulation versus a photodisruptive cutting effect. The penetration depth of the coagulated tissue volume depends beside the total delivered laser energy also on the laser wavelength. The achieved coagulation zone (volume) reduces or prevents any bleeding from the high fluency (above threshold) laser pulses that follow this step (see step e.) and create a hole or channel into the tissue layers. For a typical photodisruptive (ultra short pulsed) laser wavelength around 1050 nm (+−50 nm) the absorption length is longer than for shorter wavelengths such as used for example in a 532 nm coagulation laser (similar to SLT and ALT). Such a shorter wavelength, quasi cw (continuous wave) laser with a preferred wavelength of 532 nm or 577 nm or 810 nm can be used as a second laser source instead of the defocused photodisruptive main laser. In that configuration the second source shorter wavelength laser does not need to be focused in a highly converging beam since it only needs to reach a preferred spot size diameter of 500 μm (+−300 μm). Furthermore, if another laser is used for the photocoagulation part, than that part of the procedure can be performed before the non-invasive photodisruptive laser procedure. For example the coagulation of one or multiple treatment zones can be performed minutes or days before the channel creating procedure on a laser slit lamp setup. All the above parameter considerations for a preferred circular laser beam are also applicable to a preferred elliptical laser beam.

Step d-1. (optional) In another version, the fs-laser pattern can be fired first followed by the photocoagulation laser if necessary (if bleeding occurs). This approach minimizes treatment time. In another version, the photocoagulation laser can be left out completely to reduce system complexity and treatment time. In this case internal eye bleeding will be handled in a different way, if it occurs and if any handling is necessary at all. Small to moderate hyphemia is usually not a concern or can be addressed, e.g., by another coagulating laser workstation after the fs-laser treatment has been completed or by pressing the goniolens onto the cornea for a few seconds. When a coagulating laser is combined to prevent bleeding in case of iris root/other vessels hit, the coagulating shot is applied first over the same or larger treatment zone followed by the fs-laser pattern. This way if aimed right, the fs-laser pattern takes out the treatment zone as intended, but now has a more defined edge due to the coagulated tissue (may also be beneficial for less wound healing). If the aiming was wrong (iris root or other blood vessels) the fs-treatment zone was first coagulated and the fs-laser treated to avoid/reduce any bleeding. The coagulating shot could be a, e.g., 300 ms, 500 mW green laser shot (similar to ALT).

e. Once the threshold pulse energy is known from step b. and optional z-calibration from step c. and the optional photocoagulation (step d.) is completed, the laser will preferably automatically adjust the treatment pulse energy in a preset way relative to the threshold energy (preferably 3× to 10× the threshold energy) and preferably automatically fire a preset scanning pattern to create one or multiple holes into the desired target zone layers (e.g. through the Trabecular Meshwork or into the suprachoroidal space) within the coagulated zone, if created.

f. (optional) All steps b. to e. are preferably done in a fully automated sequence immediately following each other and parameters are optimized such that the entire laser procedure time is preferably less than 10 s.

A second method to measure and maximize the vertical angular laser beam access and therefore achieving minimal spot size at the anterior angle tissue layers of an eye. The horizontal convergence angle of the treatment laser beam is fixed to preferably 60 deg (+/−20 deg) to create a small spot size in the horizontal axis in the range of <10 μm diameter depending on the overall aberrations.

Figure 11:
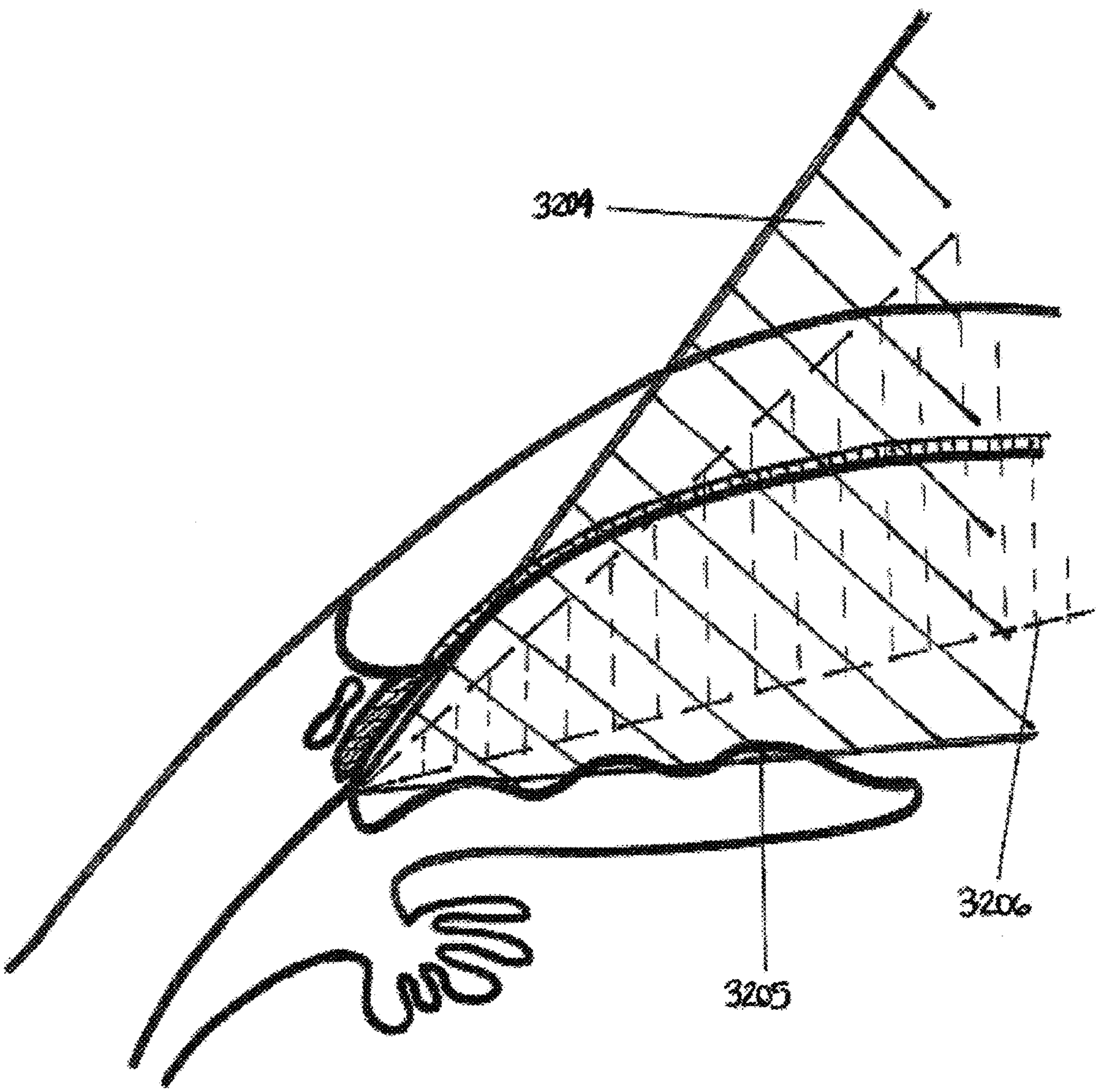
FIG. 11 shows a aiming beam and treatment laser beam focusing into the angle
Figure 12:
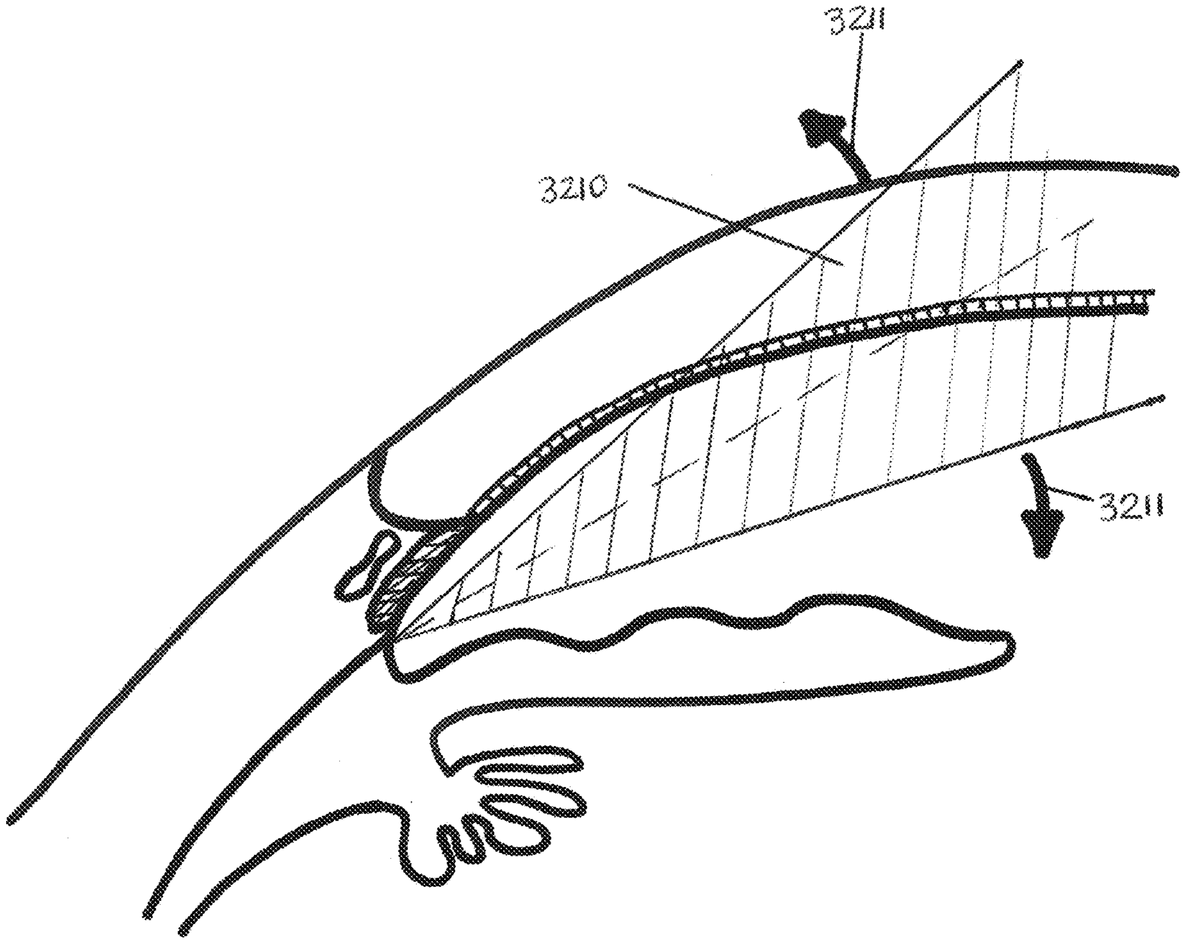
FIG. 12 illustrates an alignment motion for an aiming laser beam

Step a. The angular opening in the vertical axis is determined with the same femtosecond laser delivery system just prior to firing the photodisruptive femtosecond laser pulses by using a shape adjustable visible aiming laser beam under live observation. FIG. 11 shows an aiming laser beam 3204 being focused collinear to the planned photodisruptive treatment beam 3206 into the target tissue layer of the anterior angle of the eye. In one embodiment, this is done by changing the vertical aiming beam divergence from big to small until no light is clipping on the iris and cornea (both sides of the angle) or doing it reverse (small to big) until light starts to scatter on the outside surfaces of the angle. FIG. 11 shows the lower aiming beam envelope clipping on the iris 3205. This scattered light feedback can be observed live by the surgeon/operator or by an automated video/sensor analysis system. While the beam cone is maximized, in the same time the delivery system is preferably constantly adjusted for centration in the angle of the eye to center the focusing beam cone in the angle to achieve the setting of a maximum allowable vertical angle. This adjustment is illustrated in FIG. 12 The beam 3210 is moved in the directions 3211.

Step b. Once the maximum vertical accessibility angle to the target region has been determined the aiming beam is scanned back and forward in the z-axis (above and below the target tissue plane) using a delivery system moving lens (e.g. the main focusing lens) until the visible beam diameter on the target tissue layer is minimized. This minimum spot visualization can be performed live by observation of the surgeon through a microscope or preferably by an automated vision system. The now known z-position of the delivery system optics is now used to calibrate the z-distance of a delivery system reference point to the aiming beam focus position on the surface of the target tissue layer.

Step b-1. (optional) In another implementation, the Trabecular Meshwork treatment zone is targeted with a dual aiming beam laser approach (which could use different colors). One aiming beam targets the centre of the treatment zone (circle/ellipse) with a small spot and another one illuminates a large area or an outline of the treatment zone with the same or different color. The targeting method includes the procedure to safely stay away from the iris root to avoid bleeding. Multiple treatment areas in the field of gonioscopic view can be previewed and treated at once.

Step c. (optional) If the delivery system allows the adjustment of the vertical beam convergence angle for the photodisruptive treatment beam, then the vertical angle is now adjusted to match the maximum determined aiming beam angle from step a. This sets the treatment beam up to achieve a minimum possible vertical spot size on the target tissue layer.

Step d. (optional) Perform a coagulation step identical to the first method step d.

Step e. The control system of the laser system now calculates and then sets the optimal photodisruptive laser pulse energy based on the input from step a., b. and c. before the treatment laser is fired. The factors for this calculation are as follows: If the vertical treatment beam angle is adjustable then it has been set to the maximum vertical angle in step a. Since the horizontal focusing angle is fixed, the horizontal spot size axis is fixed as well $\omega_{0\ horizontal\ fixed}$. The vertical spot size $\omega_{0\ vertical}$ and therefore the spot size area A is according to formula 1 inverse proportional to the maximum vertical angle Θ.

$$A_{spot\ size\ area} \sim \omega_{0\ horizontal\ fixed}\,\omega_{0\ vertical} = \omega_{0\ horizontal\ fixed} M^2_{vertical} \frac{360\ \lambda}{\pi^2\ \Theta_{vertical}}$$

with $$\omega_{0\ horizontal\ fixed} = M^2_{horizontal} \frac{360\ \lambda}{\pi^2\ \Theta_{horizontal}}$$

the spot size area A becomes:

$$A_{spot\ size\ area} \sim M^2_{horizontal} \frac{360\ \lambda}{\pi^2\ \Theta_{horizontal}} M^2_{vertical} \frac{360\ \lambda}{\pi^2\ \Theta_{vertical}} \qquad \text{Formula 2}$$

The required treatment pulse energy is:

$$E_{pulse\ energy\ setting} = cE_{threshold\ pulse\ energy} \qquad \text{Formula 3}$$

with $E_{threshold\ pulse\ energy}$ being the minimum pulse energy required to achieve a photodisruptive optical breakdown on the desired tissue layer and c being a factor by which the set pulse energy needs to exceed the threshold pulse energy to achieve an efficient photodisruptive tissue effect for cutting and drilling a hole into the tissue layers. The preferred setting for c is 3 to 10. The threshold for the photodisruptive optical breakdown depends on the laser fluency F, being:

$$F_{threshold} = \frac{E_{threshold\ pulse\ energy}}{t_{pulse\ duration} A_{spot\ size\ area}} \qquad \text{Formula 4}$$

Therefore: $E_{threshold\ pulse\ energy} = F_{threshold} t_{pulse\ duration} A_{spot\ size\ area}$ or:

$$E_{threshold\ pulse\ energy} \sim A_{spot}\ \text{size area} \qquad \text{Formula 5}$$

Combining formula 2, 3 and 5 leads to:

$$E_{pulse\ energy\ setting} \sim c\ M^2_{horizontal} \frac{360\ \lambda}{\pi^2\ \Theta_{horizontal}} M^2_{vertical} \frac{360\ \lambda}{\pi^2\ \Theta_{vertical}} \qquad \text{Formula 6}$$

If the vertical angle is not adjustable, then it has been set to a fixed preferred angle of $\Theta_{vertical}$=40 deg (+/−15 deg). Depending on the measured maximum vertical accessibility angle in step a. this fixed vertical angle $\Theta_{vertical}$ is either smaller or larger than the maximum accessible angle. If it is larger than the maximum accessible angle then a clipping factor $f_{clip}$ needs to be considered that reduces the laser power on target an enlarges the spot size in the vertical axis. Including this clipping factor the laser control system calculates the required pulse energy setting for the following laser treatment according to Formula 7:

$$E_{pulse\ energy\ setting} \sim f_{clip} c\ M^2_{horizontal} \frac{360\ \lambda}{\pi^2\ \Theta_{horizontal}} M^2_{vertical} \frac{360\ \lambda}{\pi^2\ \Theta_{vertical}}$$

The beam quality factors $$M^2_{horizontal} \text{ and } M^2_{vertical}$$

depend on the sum of all aberrations of the laser system including the delivery system optics, patient interface, patient contact lens (goniolens) the interface to the eye and to some extend the condition of the cornea and anterior chamber of the eye. Most of these beam quality factors are system specific and are preferably calculated and measured. A high level of accuracy in determining those quality factors is achieved by performing photodisruptive laser threshold measurements using model and cadaver eyes on the final laser system setup. The $f_{clip}$ loss factor is also determined by performing photodisruptive laser threshold measurements using model and cadaver eyes on the final laser system setup. They are performed for a range (15 deg to 50 deg) of accessibility angles (step a.) and saved as a table within the laser control system. Once the laser procedure has started and the actual vertical accessibility angle has been determined in step a, the control system looks up the corresponding $f_{clip}$ loss factor and calculates the final laser pulse energy setting $E_{pulse\ energy\ setting}$ according to formula 7.

Step f. After the control system sets the treatment laser pulse energy, the laser will preferably automatically fire a preset scanning pattern with reference to the laser beam alignment in step a. and the z-calibration in step b. to create one or multiple holes into the desired target zone layers (e.g. through the Trabecular Meshwork or into the suprachoroidal space) within the coagulated zone, if created.

Step g. (optional) All steps a. to f. are preferably done in a fully automated sequence immediately following each other and parameters are optimized that the entire laser procedure time is preferably less than 10 s.

A third method for delivering a particular pulse sequence of circular or elliptical spot size femtosecond laser pulses to create a hole(s) or channel(s) into the tissue layers of the anterior angle of an eye. The method describes a scanning pattern that can for example be applied during the laser firing in the first method step e. or the second method step f. to create the hole and channel into the desired target tissue layers. The method is as follows:

The treatment area (this is the area within which a hole connection between the anterior chamber and Schlemm's canal through the Trabecular Meshwork is created) can be a circle of about 50 μm to 500 μm diameter. The treatment circle can also be a large ellipse, e.g., 400 μm by 50 μm to make it easier (more likely) to hit the Schlemm's canal for sure. Treatment circle means here always that the laser spots are scanned over the entire circular/elliptical area.

Step a. The beam (round or elliptical focus) will be scanned in a circular pattern to create the hole and channel into the desire target tissue layers. The preferred starting cutting circle diameter is 250 μm+/−100 μm. The preferred spot separation is 10 μm+/−7 μm. The first circle is cut at a z-alignment that brings the focus plane of the treatment laser beam within +/−10 μm of the surface plane of the target tissue layer.

Figure 13:
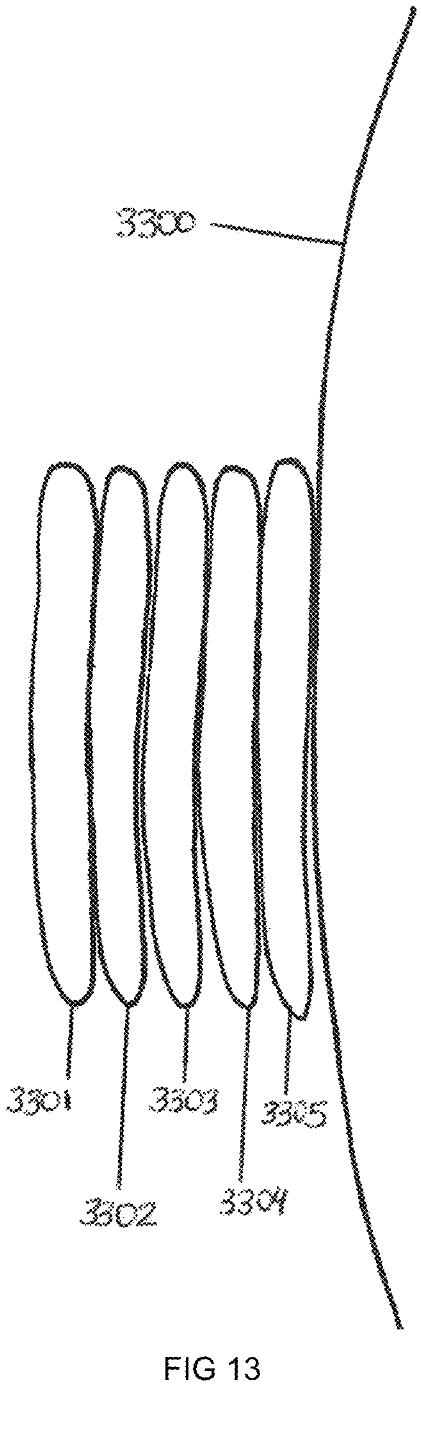
FIG. 13 shows a circular laser firing pattern in the anterior angle tissue layers
Figure 14:
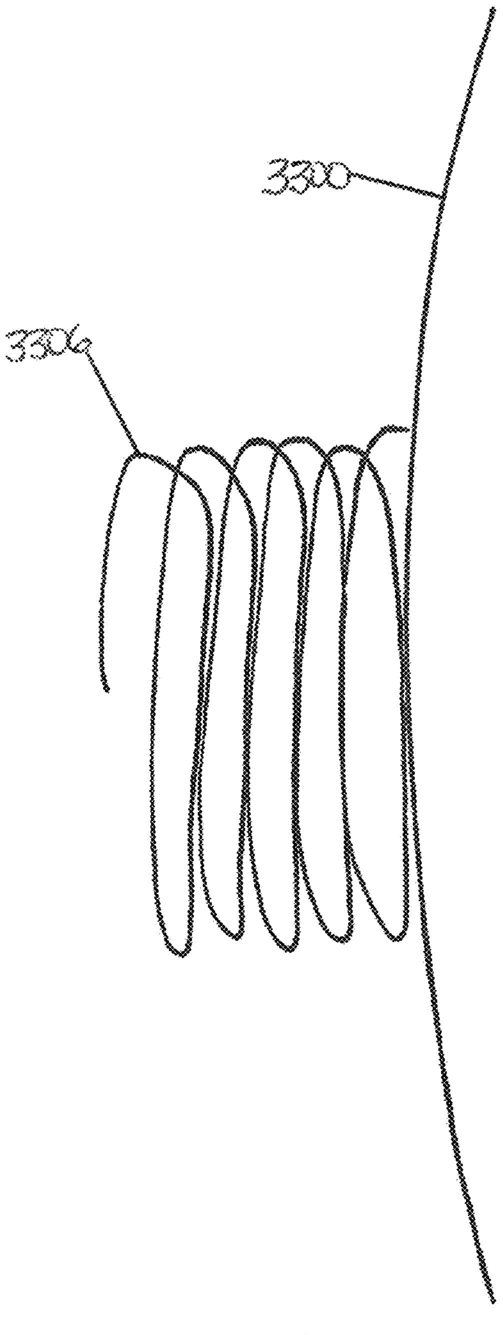
FIG. 14 shows a corkscrew laser firing pattern in the anterior angle tissue layers

Step b. Several additional circles (preferably 10+/−7 more) are being cut successively moving deeper into the tissue layers. Each new circle is preferably focused 7 μm+/−5 μm deeper than the last see FIG. 13 or the circles are continuously going deeper into the tissue in a corkscrew type of scanning pattern, see FIG. 14 with the same slope (7 μm deeper per revolution).

Step c. (optional) The laser focus plane is moved back up to the original surface of the top tissue layer and the laser is now scanned over the entire circle area in a raster or spiral pattern with a preferred spot separation of 5 μm+/−3 μm. Similar to step b the focus plane is then lowered by 7 μm+/−5 μm and the same areal cutting is repeated. This is also repeated preferably 10 times.

Step d. The focus plane is moved back up to the original surface plane of the top tissue layer and the laser is now repeats the scan pattern from step but with a preferably 30 μm+/−20 μm reduced diameter. This means for the preferred case a new concentric circle diameter of 220 μm. Furthermore the amount of cutting circles or corkscrew rotations is now increased by preferably another 10 to a total of 20 circles. This results in a preferred cutting cylinder depth of 20×7 μm=140 μm.

Step e. (optional) repeat step c. with a reduced diameter and extended depth according to step d.

Figure 24:
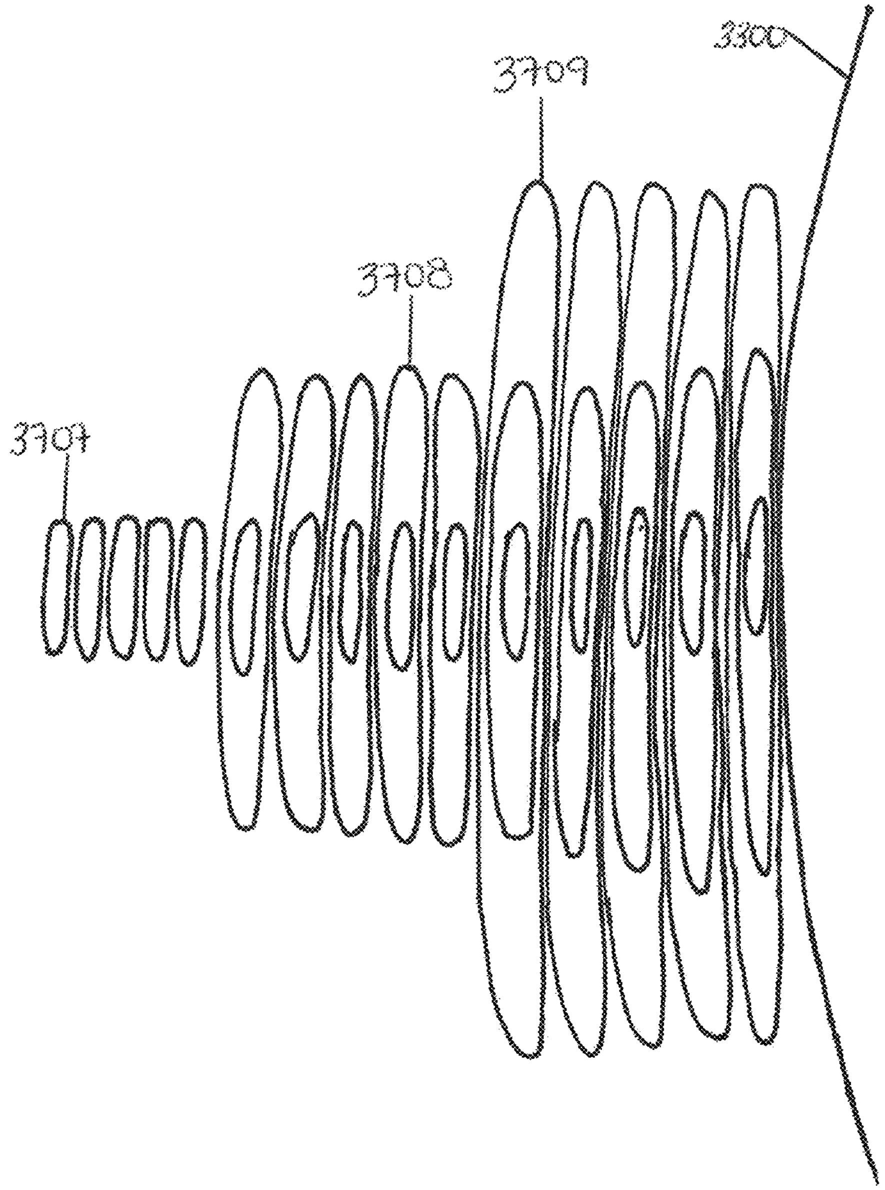
FIG. 24 illustrates a laser firing pattern

Step f. Repeat step d. and step c. while further reducing the diameter and extending the cutting depth until the desired hole or channel depth has been achieved. FIG. 24 shows an example of the total scanning pattern after 3 cycles with different diameters 3709, 3708, 3707 and depths have been completed. The preferred cutting channel depth for the Trabecular Meshwork are in the range of 100 μm to 300 μm while the preferred channel length for an access channel into the suprachoroidal space is between 400 μm and 3 mm. Other desired target areas will have other preferred channel lengths.

Figure 23:
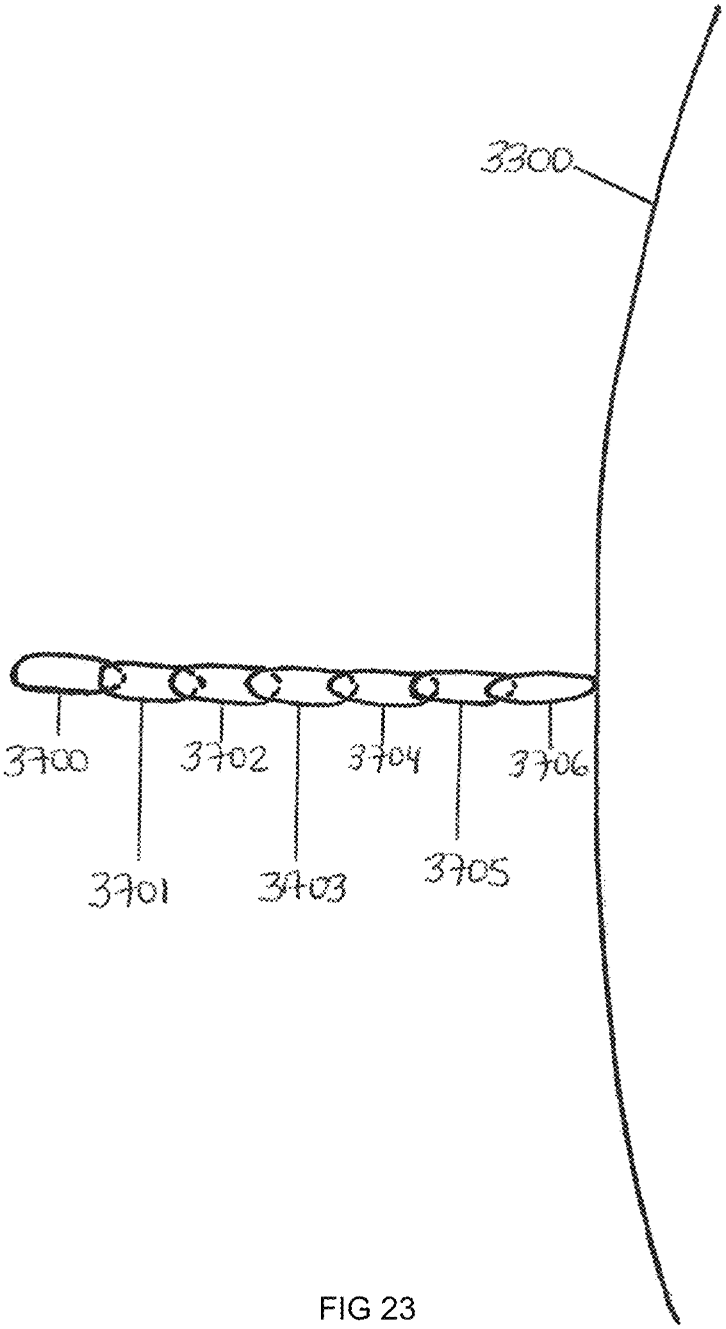
FIG. 23 illustrates a laser firing pattern

Step g. (optional) The laser pulse energy is increased (preferably by a factor of 2+/−0.8) and the laser is fired preferably 10 times back and forward along the central z-axis of the holes/channel with a scanning depth amount that is equal to the hole/channel length. FIG. 23 shows the overlapping linear micro destruction zones 3700 to 3706 of the individual laser pulses after the first z-scan. 3300 represents the top tissue layer in the anterior chamber angle region. This step clears any remaining tissue debris out of the channel. This step can be repeated a few times with a few seconds of pause in between to allow the cavitation bubbles to disappear.

Step h. (optional) The cutting sequence described in step a to step g creates a slight cone shaped channel getting smaller diameter as the channel progresses deeper into the tissue layers. This scanning sequence and cone angle can be reversed by starting with the smallest circle diameter and going outwards while going deeper.

Step h-1. (optional) As an alternative to the outside-in scanning sequence described in Steps a through g, the beam (round or elliptical focus) may be scanned in a raster, spiral or circular pattern to create the hole, with multiple circles in z-axis being cut either from the inside (Schlemm's canal depth around 120 μm) out, or in several sequences from the outside in (big circle completely scanned with individual laser pulses with a depth setting of e.g. 30 μm deep, coming out at 10 μm per complete circle, then smaller circle starting at 60 μm deep coming out at 10 μm circle to circle distance and so on). The inside-out scanning approach initiates photodisruption at or near the interface between Schlemm's canal and the Trabecular Meshwork, thereby facilitating the formation of a drainage connection to Schlemm's canal at the outset of the procedure. The outside-in and inside-out scanning directions may also be combined to ensure complete channel formation through the Trabecular Meshwork.

Figure 15:
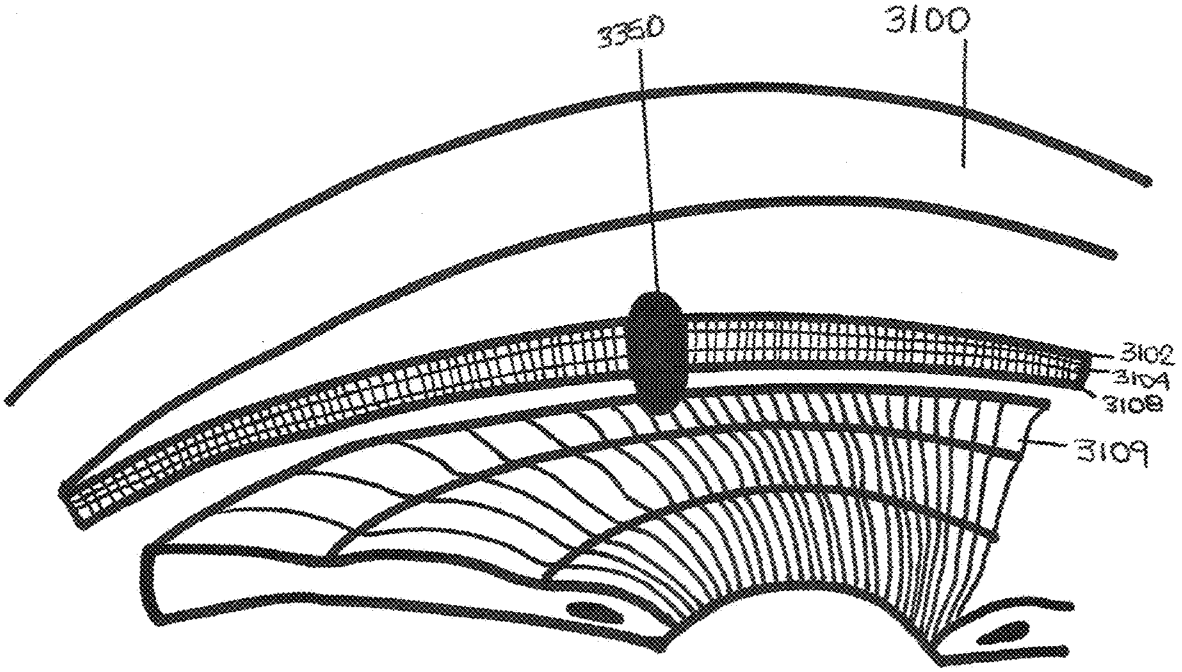
FIG. 15 shows a elliptical photocoagulation zone in the angle of an eye

Step i. (optional) The channel can also be cut with a cross sectional shape of an ellipse. Instead of circles the laser is scanned in elliptical shapes. For example an ellipse with the long axis being vertical has the advantage of easier assuring a channel connection to Schlemm's canal since it runs somewhere behind the Trabecular Meshwork along the horizontal plane see FIG. 15.

Step i-1. The treatment circle can also be a large ellipse e.g. 400 μm by 50 μm to make it easier (more likely) to hit the Schlemm's canal. Regardless of whether a circular or elliptical treatment shape is employed, the laser spots can be scanned over the entire circular/elliptical area at each depth level before advancing to the next depth.

Step j (optional) In step a. instead of placing the first circle z-depth at +/−10 μm within the top surface layer of the tissue, the first cutting plane is adjusted 20 μm below the tissue surface. This thin tissue layer can still be sufficiently penetrated by the laser energy and the resulting cavitation bubble below the surface explodes the above tissue layers away more effectively. This method variation requires a preferably 2 times larger laser pulse energy setting and is therefore not available for certain low cost, low power laser systems.

Step j. To create multiple holes and channels step a. to step i. are repeated at a different locations.

A forth method describing a laser scanning pattern to create a channel into the desired tissue layers of the anterior angle of the eye using a low cost minimal complexity laser delivery system.

Step a. For a low cost laser delivery system that only contains a z-axis scan ability, the channel can be cut by only performing step g. from the third method described above see FIG. 23. The amount of back and forward scanning cycles is now increased to preferably 50 times+/−30 times.

A fifth method to automatically select and target multiple treatment zone(s).

Step a. Use a vision system to visualize certain landmarks in the tissue layers of the anterior angle of the eye, such as for example the iris root, Schwabe's line or scleral spur.

Step b. (optional) let the surgeon select the desired target areas and channel size parameters in reference to the visualized landmarks.

Step c. (optional) the control system selects one or multiple target areas automatically based on the predetermined user preference settings.

Step d. the surgeon activates the automatically guided laser alignment and treatment sequence to create one or multiple channels.

Step e. (optional) The control system includes a tracking system that continuously verifies the position of the reference landmarks and adjusts the laser beam position as necessary to compensate for any patient/eye movements.

The system can further include automatic computer-controlled avoidance of treatment areas (in case surgeon has chosen a bad area). This can include a green/red light indication to signal whether the selected treatment zone is acceptable or should be repositioned.

Step f. The laser firing sequence follows the principles of the first to the third methods described above.

A sixth method using a gonio lens or patient interface to increase the vertical anterior angle accessibility angle by applying a controlled and directional amount of pressure in combination with the photodiruptive laser procedure.

Furthermore particularly in the second method, the gonio lens (custom patient interface) can be temporarily pressured against the cornea (similar to dynamic gonioscopy) in a way that opens the angular access significantly in the target zone and therefore allowing greater access. This step would be done just seconds prior to or during the second version method (above) but is also possible prior to the first version. If used with the first version (pre measurement of angle anatomy with other device before laser treatment—minutes to days before—) than the opening effect of a specifically controlled pressuring procedure is measured. With this information the gonio/patient interface pressure procedure can be repeated during the laser treatment and the effect is now known and therefore can be considered in the setting of the femtosecond laser and delivery system tuning for that patient.

A first system being a specific contact interface designs that includes gonio lens functionality, creates high angular access to the anterior chamber angle and minimizes beam aberrations to effectively deliver the highly converging laser beam into the anterior angle of the eye.

Figure 6:
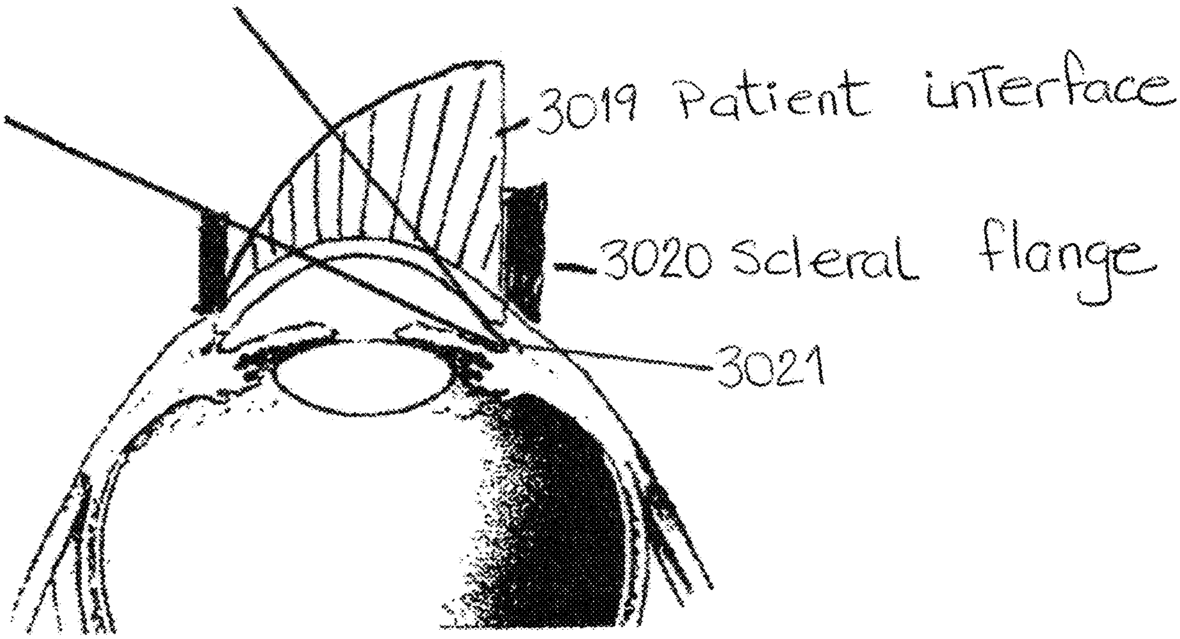
FIG. 6 illustrates a laser beam path using a direct gonio lens
Figure 7:
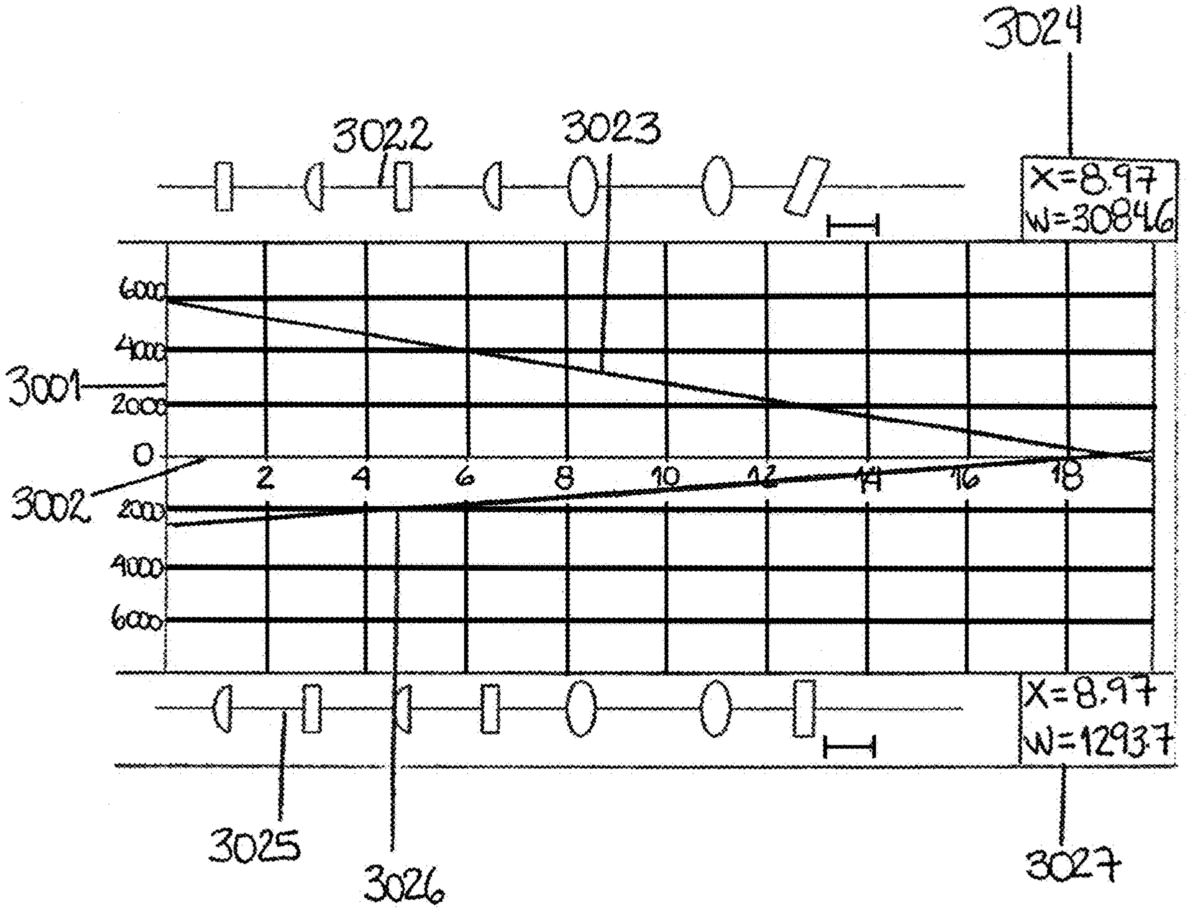
FIG. 7 shows a simulated laser beam with different focusing characteristics in the horizontal and vertical axis

A direct view gonio lens that covers the entire cornea and in one implementation also includes a flange see FIG. 6 and in another implementation has a suction ring that covers the limbus and part of the sclera to produce better eye stability. This direct lens will allow maximum angular access to the eye (anterior angle), which will enable a small spot size for the fs-laser as is desired to achieve optical breakdown in the tissue (Trabecular Meshwork). However it will require a significant targeting angle between the laser beams approaching the eye and the normal axis (axis of eye view direction) of the eye. This angle will be in the order of 45 degrees as illustrated in FIG. 6. This allows easy access to the nasal and the temporal part of the anterior angle segments. The superior and inferior parts are more challenging with this gonio lens in both a slit lamp and operation room delivery system version.

Figure 25:
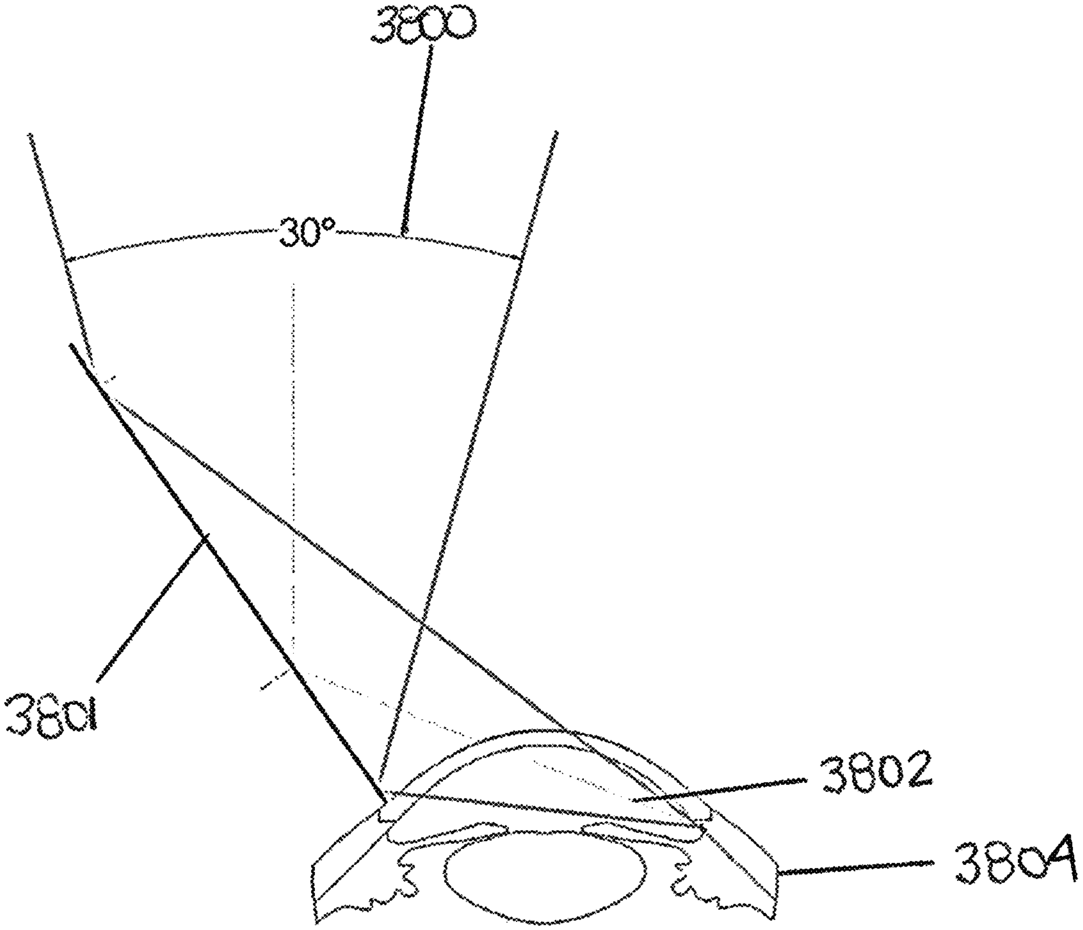
FIG. 25 illustrates the laser beam path of a specific mirror gonio lens
Figure 26:
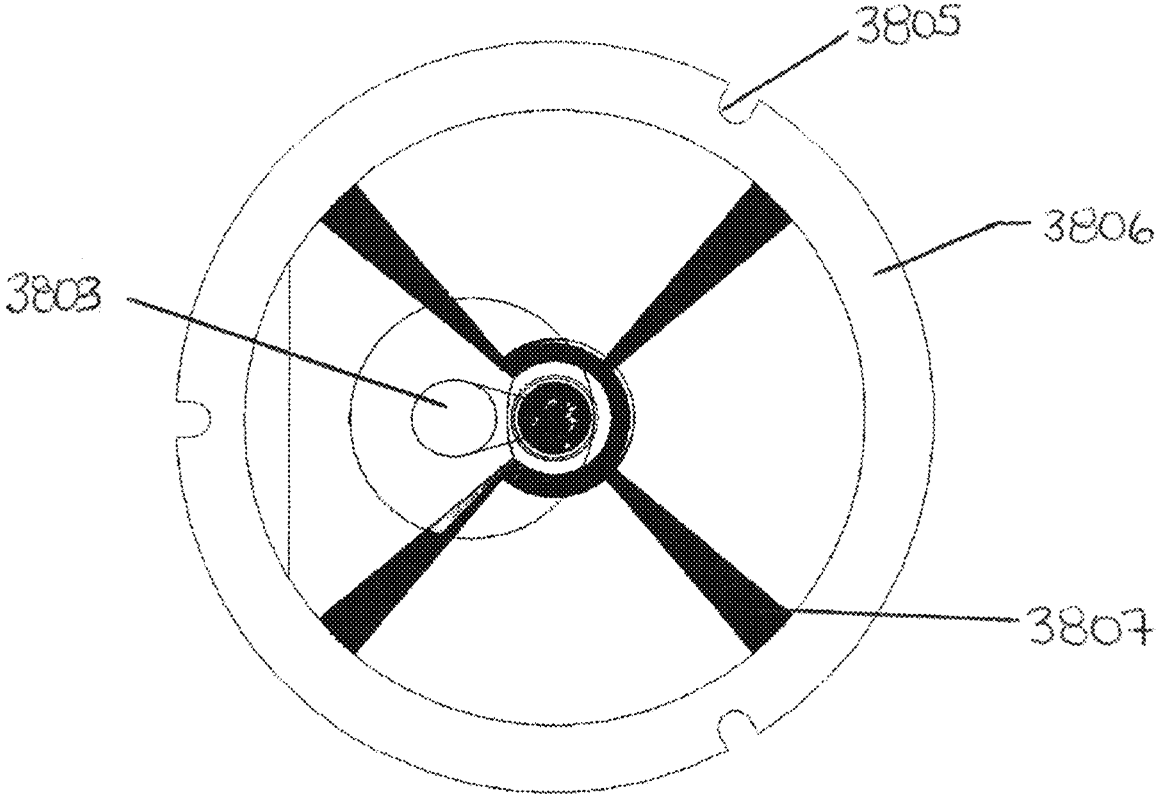
FIG. 26 illustrates a detailed patient interface design
Figure 27:
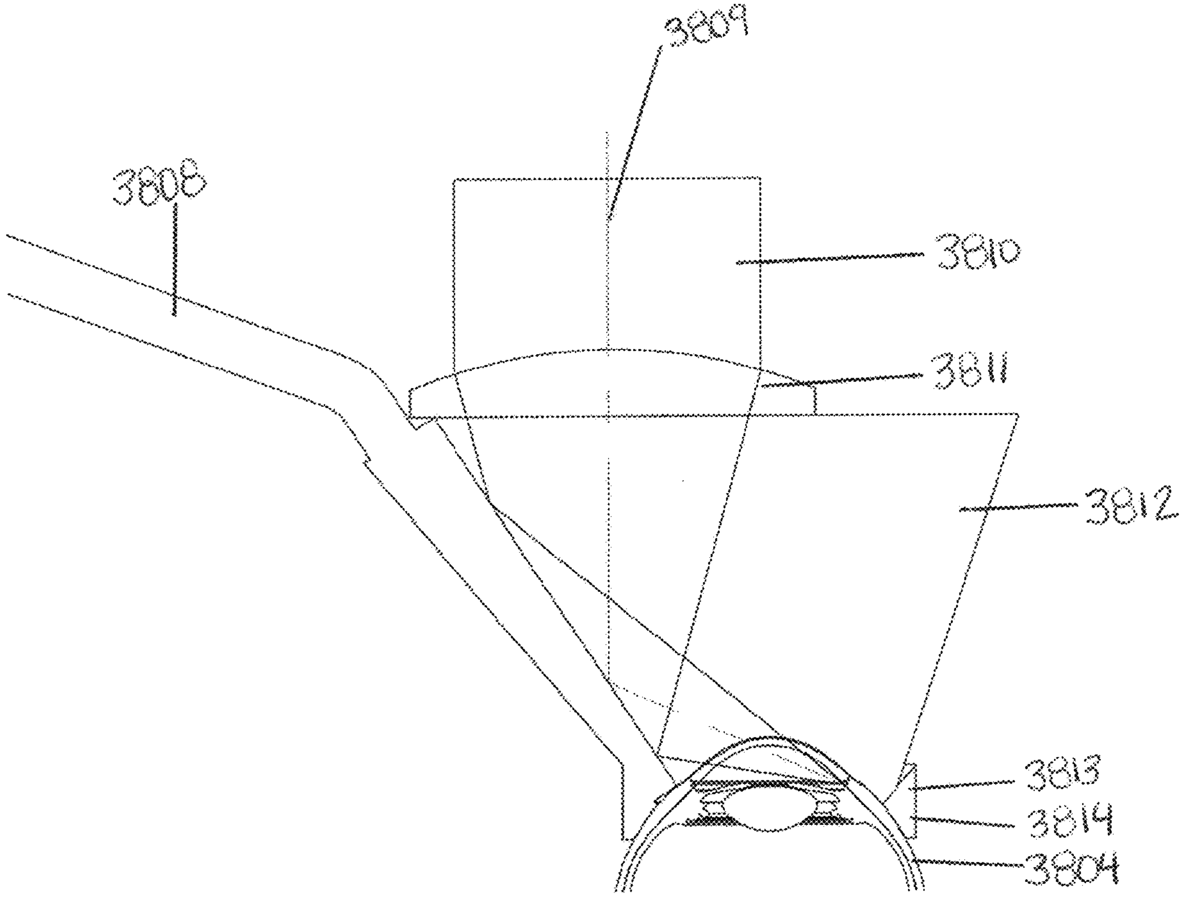
FIG. 27 illustrates a detailed patient interface design
Figure 28:
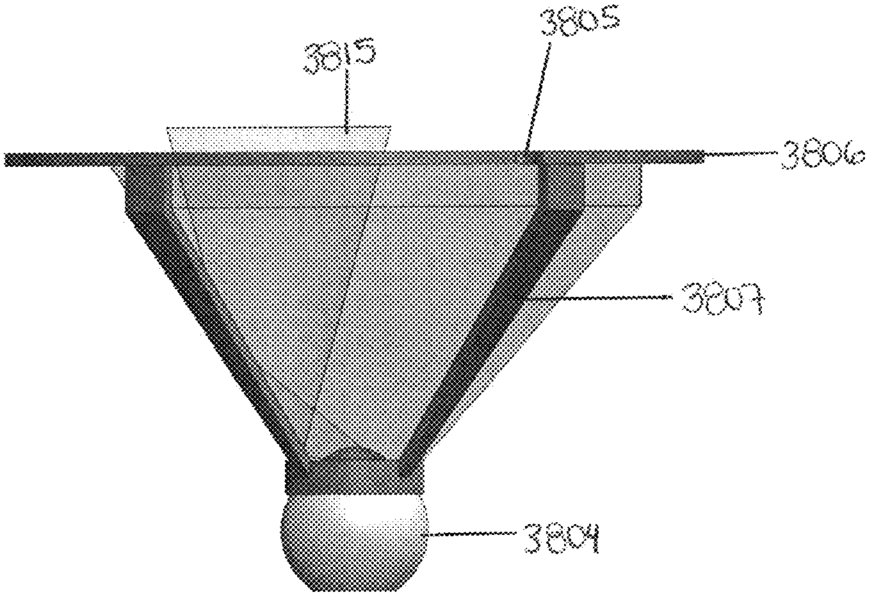
FIG. 28 illustrates a detailed patient interface design
Figure 29:
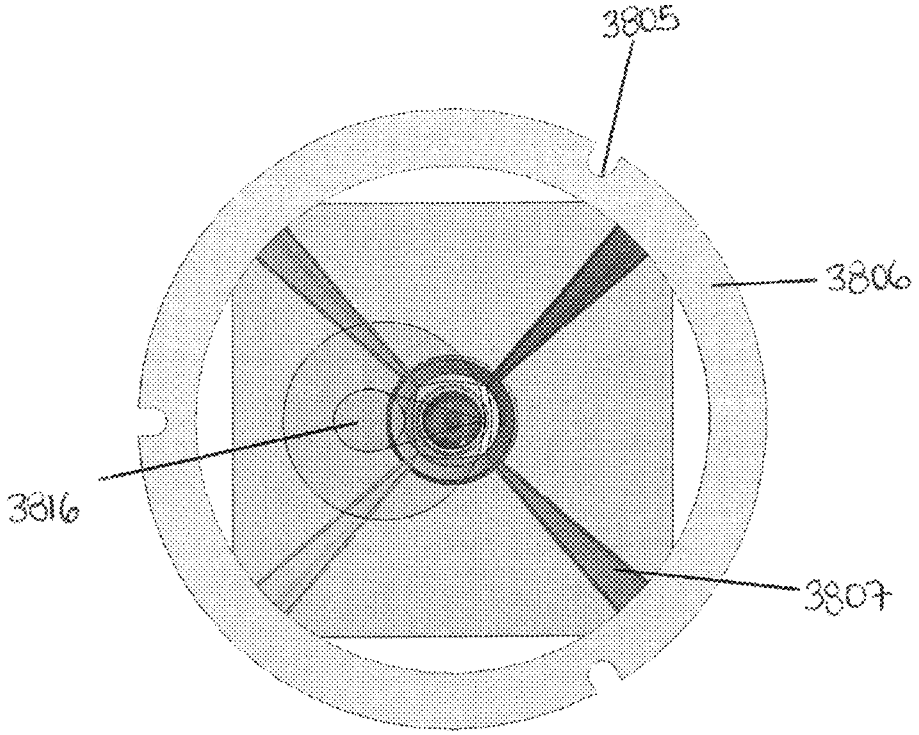
FIG. 29 illustrates a detailed patient interface design
Figure 30:
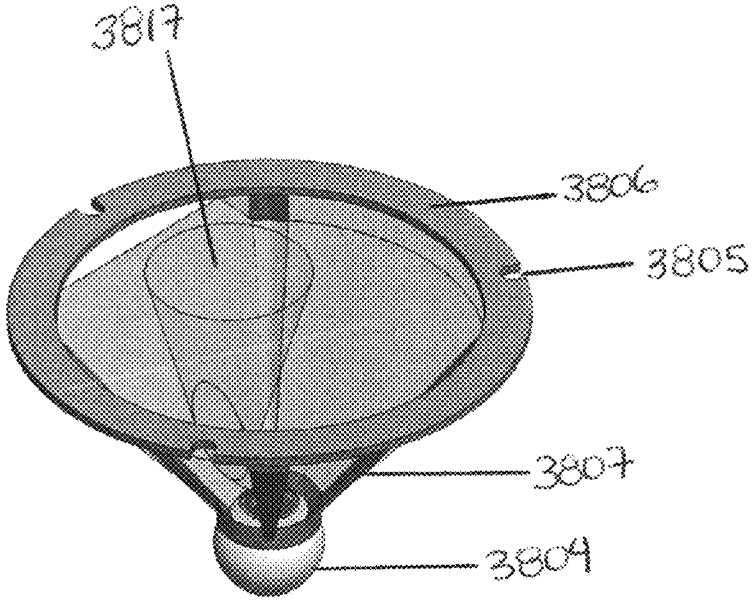
FIG. 30 illustrates a detailed patient interface design

Another preferred implementation to access the entire anterior angle rim is using a mirrored gonio lens that allows the visualization and laser beam to come vertically, parallel to the main optical axis of the eye. See FIG. 27. This diagram shows a handheld custom one mirrored lens similar to a SLT Latina lens, but optimized for maximum angular access of the laser beam. In this lens the beam path opening (convergence angle) can reach 30 deg as illustrated in the beam only view in FIG. 25. 3081 represents the mirror, 3800 the 30 deg converging laser beam. FIG. 27 shows that this lens includes a scleral flange 3813 that increases stability and eye fixation. A suction channel inside the flange 3814 further increases eye stability. The lens is placed on the cornea using a liquid gel as an interface between the lens and the cornea to avoid any air gaps or bubbles. This lens also includes a lens on the top surface 3811 that is offset to match the laser beam path centrally. Other views of the same design are found in FIGS. 37, 39, 41, 42 45, and 46. This lens further increases the focusing convergence and allows the laser delivery system to propagate a less converging laser beam. This feature reduces the delivery system complexity. Furthermore this top lens allows a normal (vertical) laser beam approach towards the eye and is therefore easier implemented in all three configurations (slit lamp, operating microscope and modified femtosecond cataract workstation delivery system configuration). This gonio lens allows simple access to the entire 360 degree circle of the anterior angle simply by rotating the lens. Therefore multiple holes in the Trabecular Meshwork or other desired targeting zones around the angle of the anterior chamber can be easy created with minimal scanning abilities of the femtosecond delivery system.

A second system being a specific contact interface designs that includes gonio lens functionality, creates high angular access to the anterior chamber angle and minimizes beam aberrations to effectively deliver the highly converging laser beam into the anterior angle of the eye.

Figure 17:
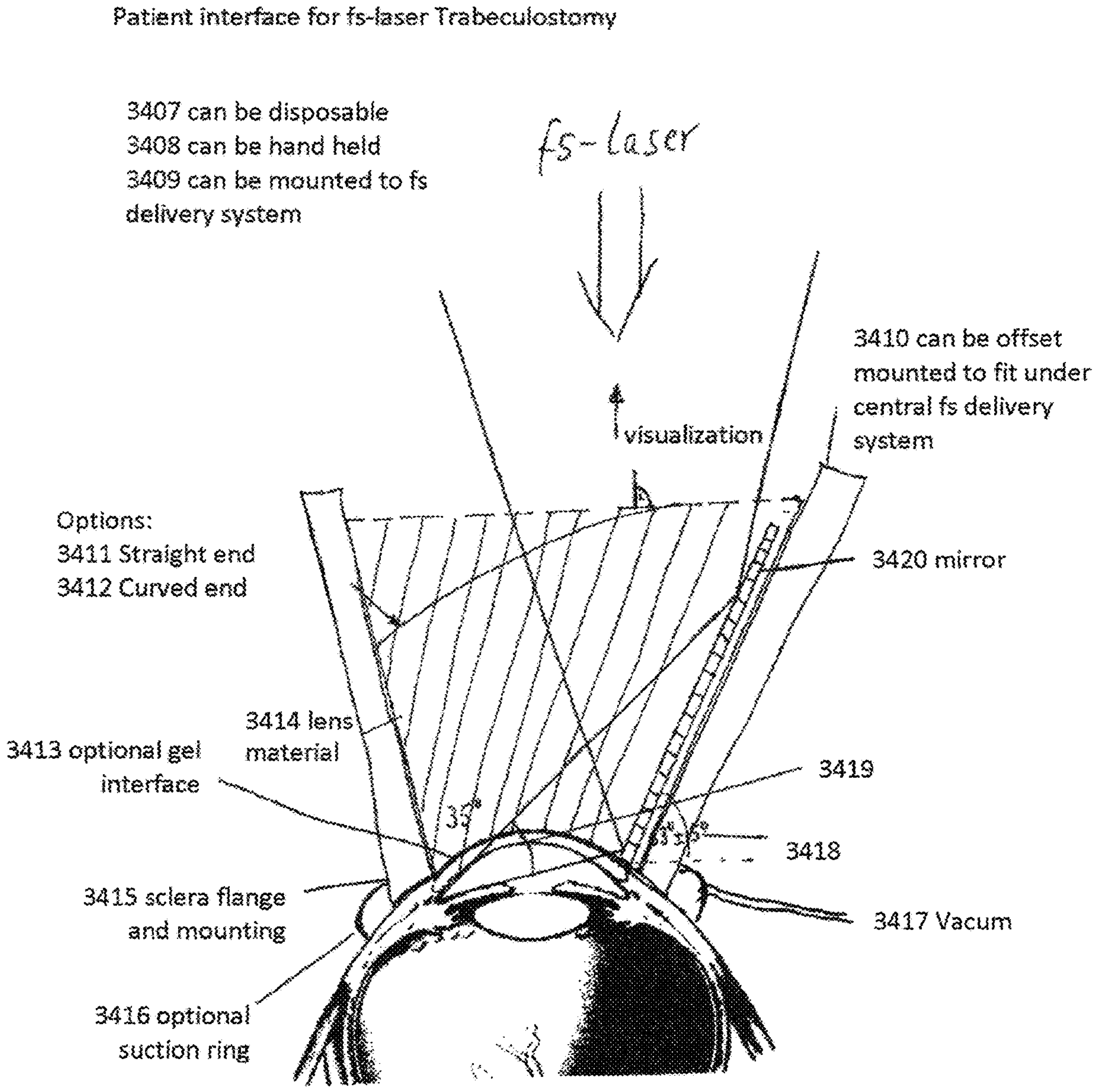
FIG. 17 illustrates a detailed patient interface design

FIG. 17 shows a mirror gonio lens design with novel features to allow laser beam access to the anterior angle at high degrees of convergence. These features include a scleral flange . . . and a suction ring for increased fixation, a single mirror tilt angle to horizontal of 63 deg+/−5 deg for an outer housing that can interface to a delivery system in an offset way and that can be made disposable or handheld. The inner lens material can end in a plane horizontal surface or can end in a curved convex lens shape, adding magnification to the gonio lens design. This lens further increases the focusing convergence and allows the laser delivery system to propagate a less converging laser beam. This feature reduces the delivery system complexity.

The device includes a custom goniolens that allows the transfer of the highly divergent fs-laser beam and can also withstand the coagulation beam.

A third system being a specific patient interface designs that connect the laser delivery system to the eye and incorporates a specific gonio lens design that allows photodisruptive laser access to the anterior angle of the eye.

Figure 16:
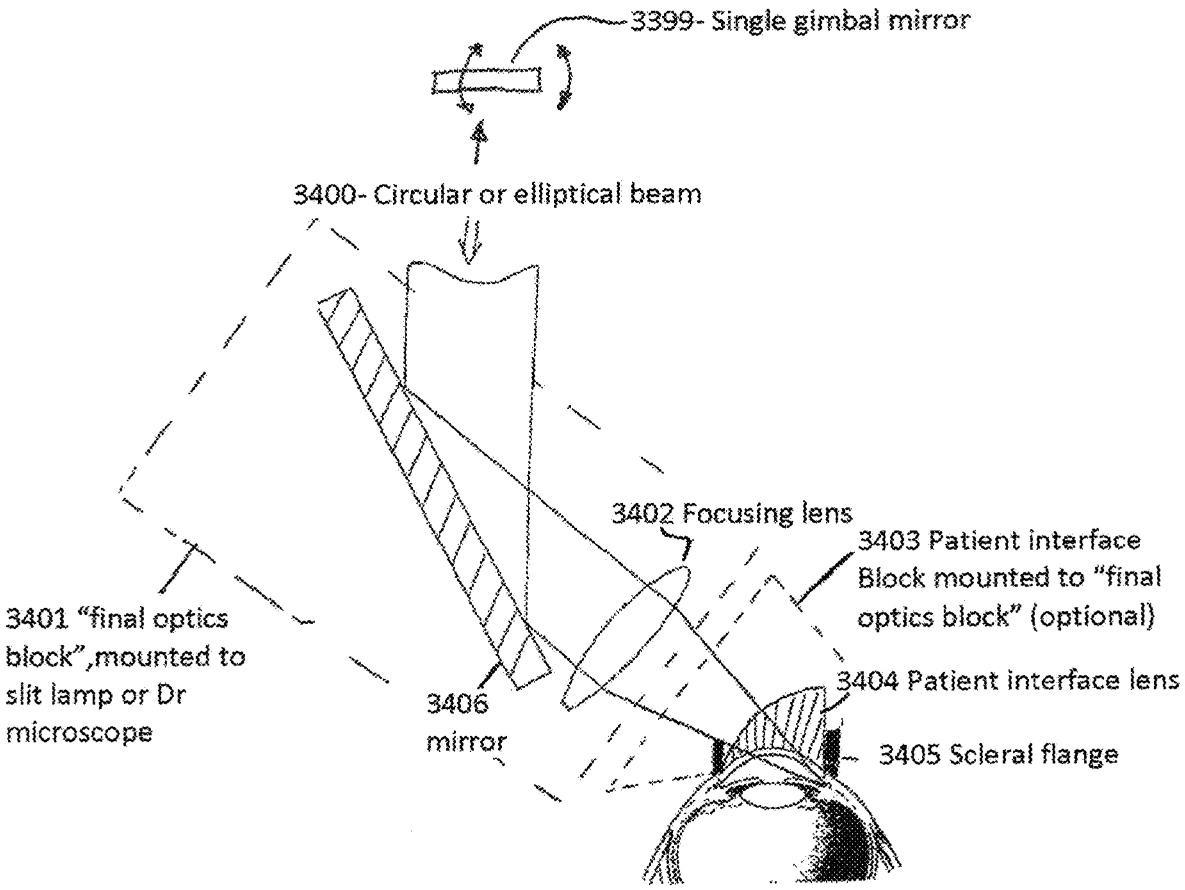
FIG. 16 shows a detailed delivery system design

FIG. 16 also shows the design of a custom direct view gonio lens/patient interface that can be mounted to the "final optics block" or can be handheld in a simpler manual version.

A fourth system being a specific patient interface designs that connect the laser delivery system to the eye and incorporates a specific gonio lens design that allows photodisruptive laser access to the anterior angle of the eye.

Figure 33:
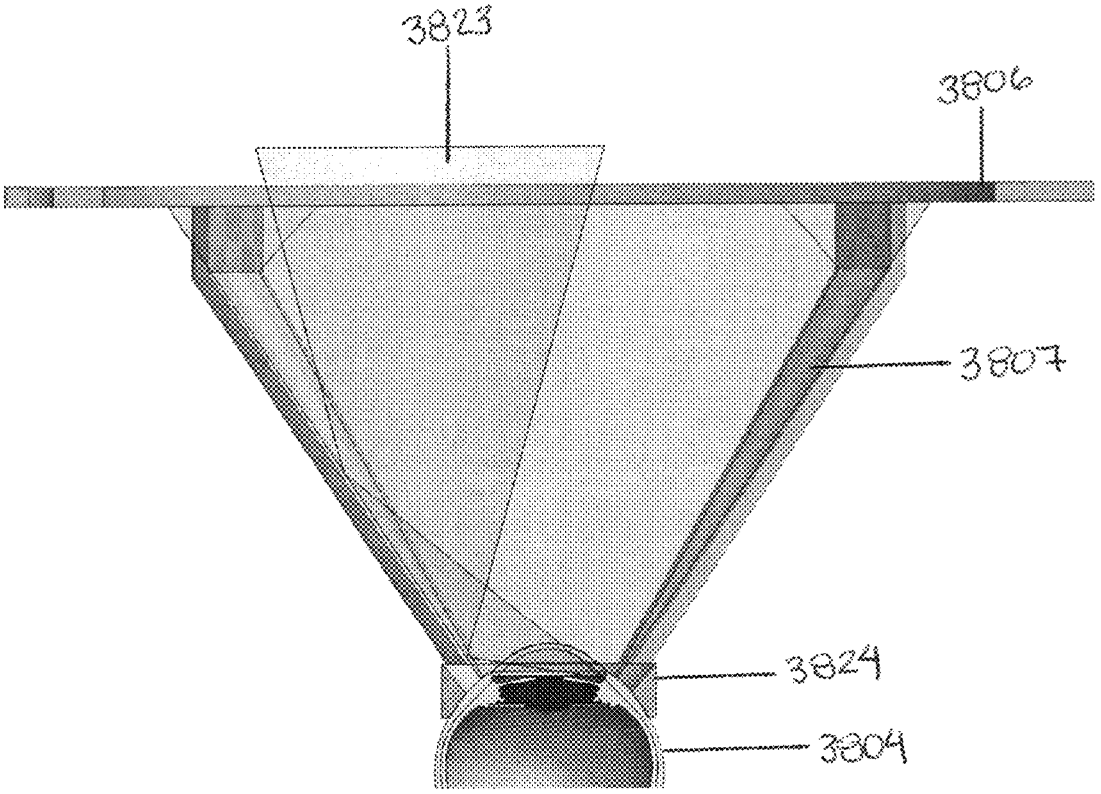
FIG. 33 illustrates a detailed patient interface design
Figure 34:
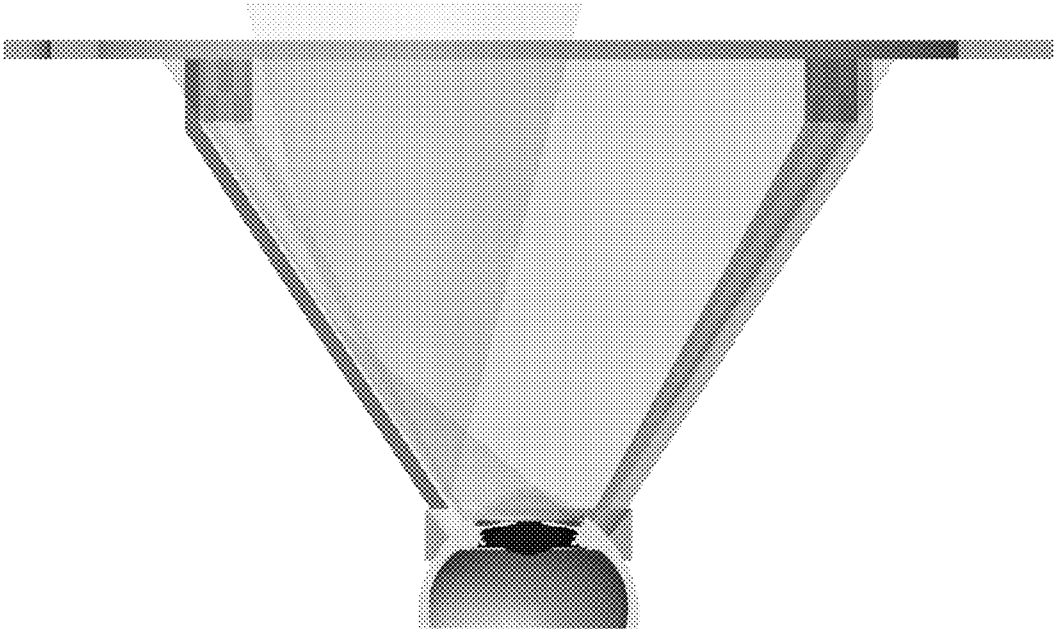
FIG. 34 illustrates a detailed patient interface design
Figure 35:
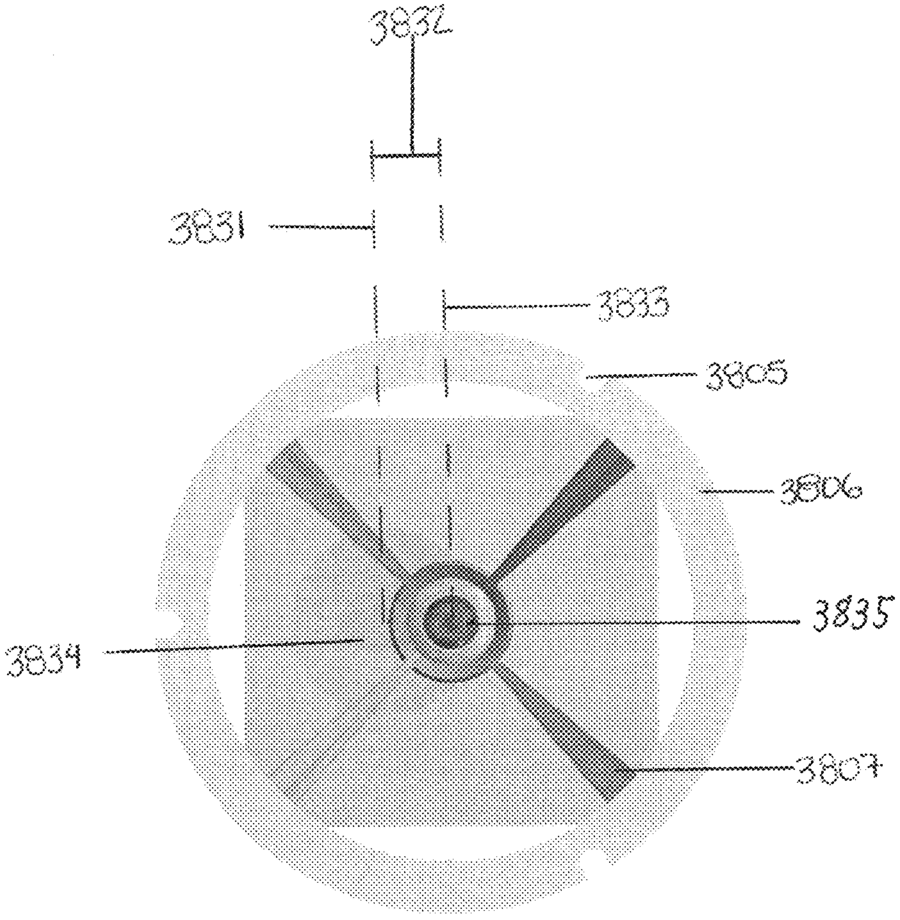
FIG. 35 illustrates a detailed patient interface design

FIG. 33 shows a cross-section of a specific interface that incorporates single large mirror, a scleral flange and optional suction channel. It allows a laser convergence access angle of 30 deg. The laser beam in its most centered focusing position relative to the anterior angle enters the patient interface vertical with an offset to the central line of the eye. This design includes a mounting ring on top see FIG. 35 that incorporates indexing, reference and locking features 3805 to be connected to a delivery system. This patient interface is used to connect to a surgical delivery system of a photodisruptive laser system. It can also be adapted to an existing medical laser system such as used for femtosecond LASIK or femtosecond laser assisted cataract surgery. FIGS. 26,28,29,30,31,32,34 and 40 show different cross-sections and views of the same patent interface design. This patient interface is preferably made disposable. Furthermore since this patient interface allows besides the mirror 3834 direct access to the entire cornea from straight above without going through the mirror, see FIG. 35, this design allows multiple use such as a combined femtosecond cataract procedure (cutting a capsulotomy, cornea incisions and lens fragmentation) with a femtosecond glaucoma procedure (cutting one or multiple channels into a target region in the anterior angle of the eye) or a femtosecond LASIK combined with a femtosecond glaucoma (cutting one or multiple channels into a target region in the anterior angle of the eye). The preferred method to use this design in a multiple use surgery is by incorporating a lateral offset shift mechanism into the delivery system docking part. This offset shift mechanism allows the delivery system docking feature FIG. 35, 3805 to be mounted to the patient interface in 2 positions with an offset of FIG. 35, 3832 For the glaucoma procedure part the mirror is centered relative to the delivery system 3831. For the other surgery part the cornea is centered to the delivery system 3833. The combination procedure can be performed in any desired order. This offset shift mechanism is preferably activated by a motor, solenoid or spring force energy.

Another custom goniolens version is integrated into a custom patient interface, that connects a patient's eye to a fs-laser system that also performs laser assisted cataract procedures. This gonio lens can be mounted into such a patient interface in a way, that it either mechanically swings in place or out of place or both so that such a cataract photo disruptive laser system (typically used to create capsulotomies/capsulerexis, lens fragmentation and cornea incisions) can also be expanded in its purpose to also create holes in the Trabecular Meshwork either before the cataract laser treatments or after.

A fifth system being a specific patient interface designs that connect the laser delivery system to the eye and incorporates a specific gonio lens design that allows photodisruptive laser access to the anterior angle of the eye.

Figure 36:
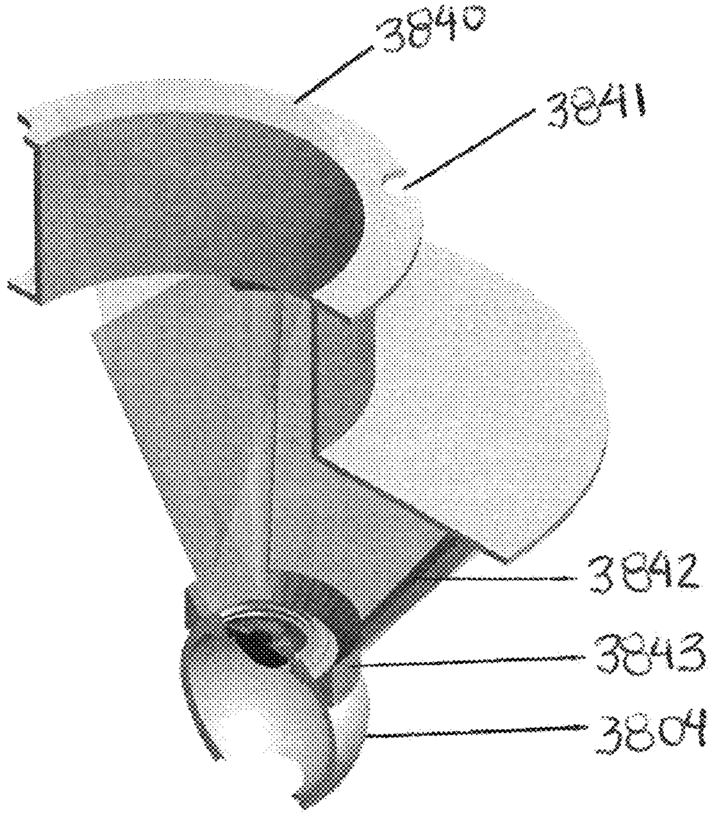
FIG. 36 illustrates a detailed patient interface design
Figure 37:
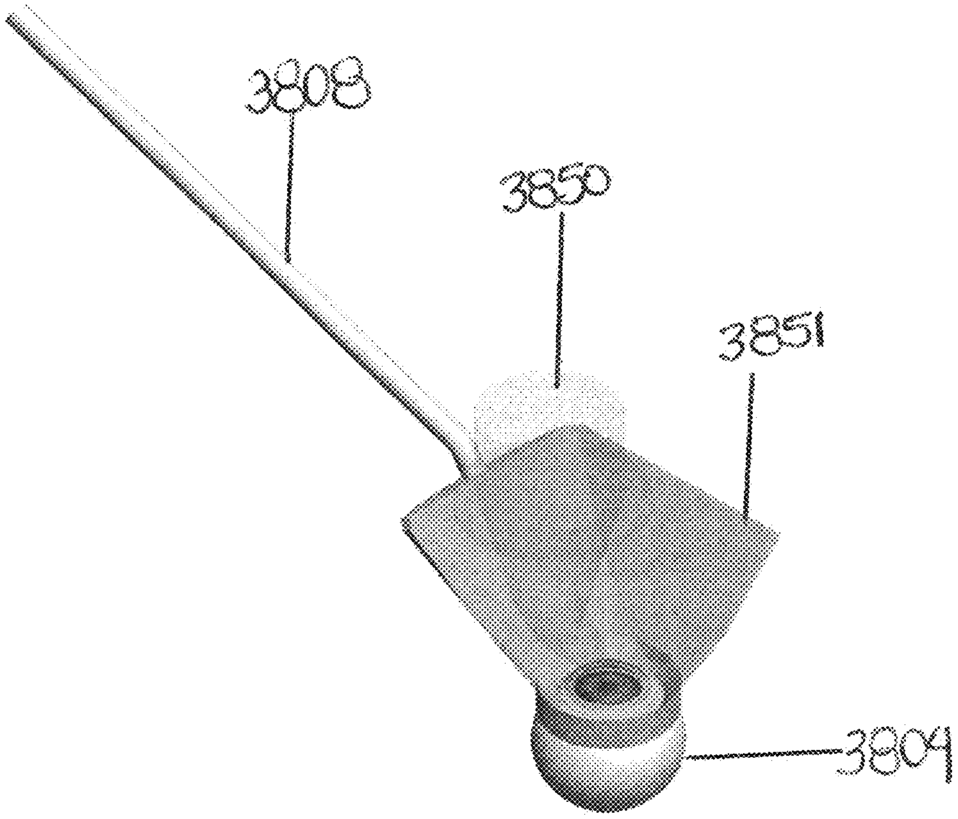
FIG. 37 illustrates a detailed patient interface design
Figure 38:
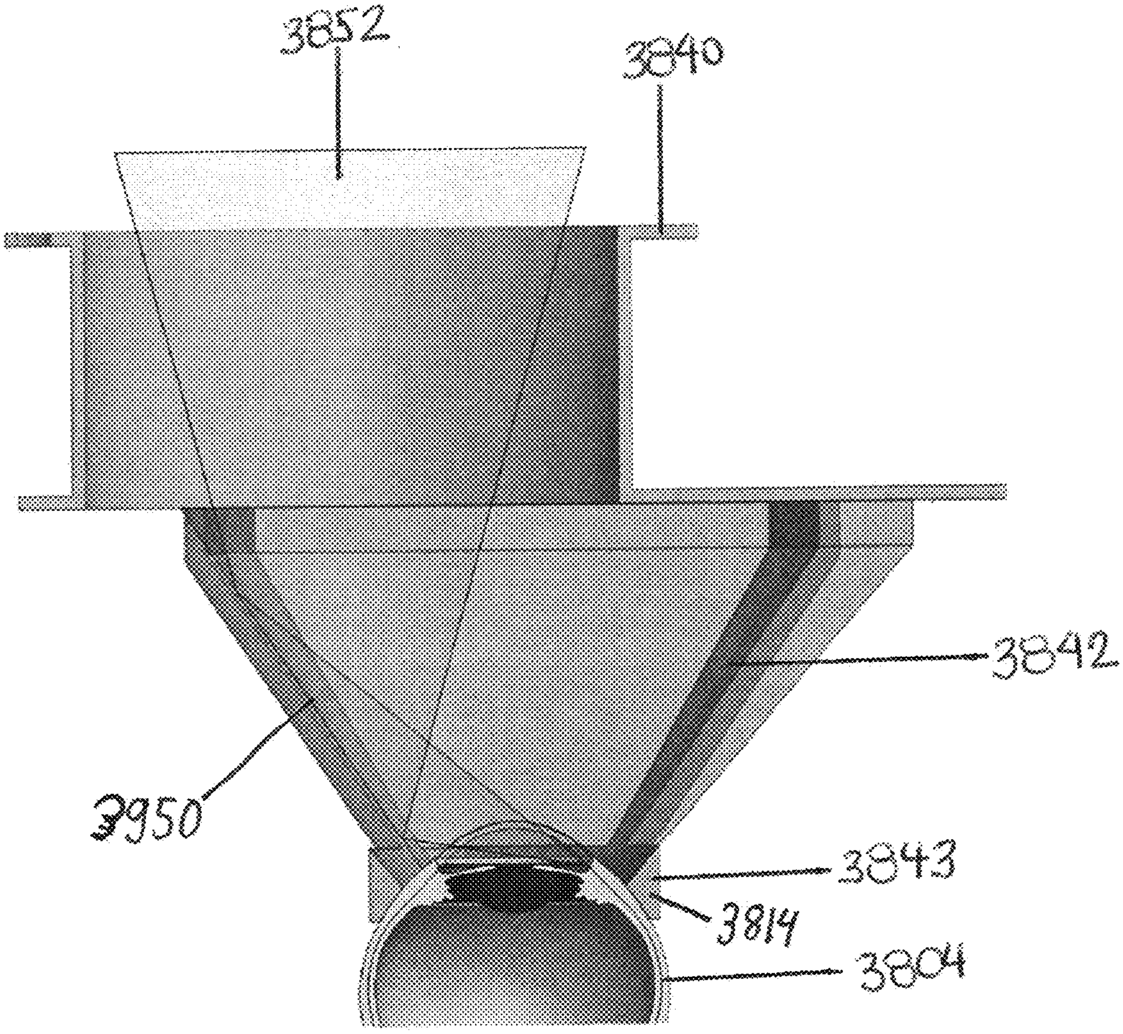
FIG. 38 illustrates a detailed patient interface design
Figure 39:
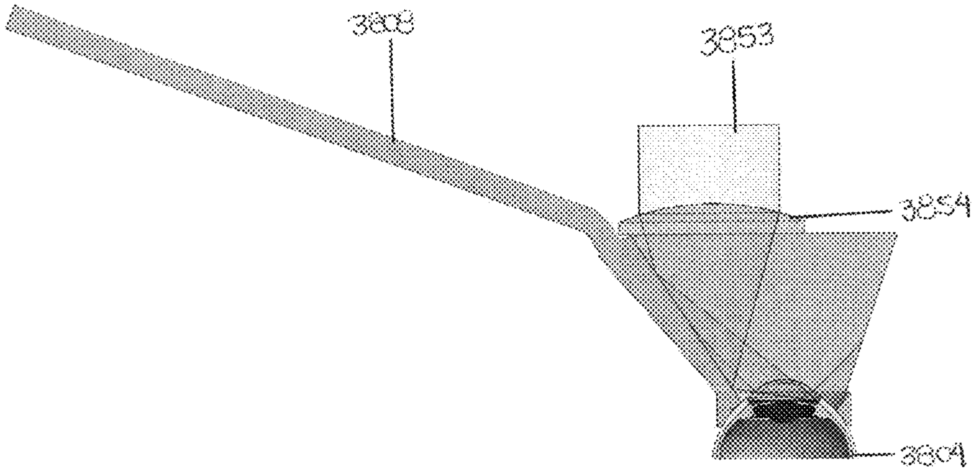
FIG. 39 illustrates a detailed patient interface design
Figure 40:
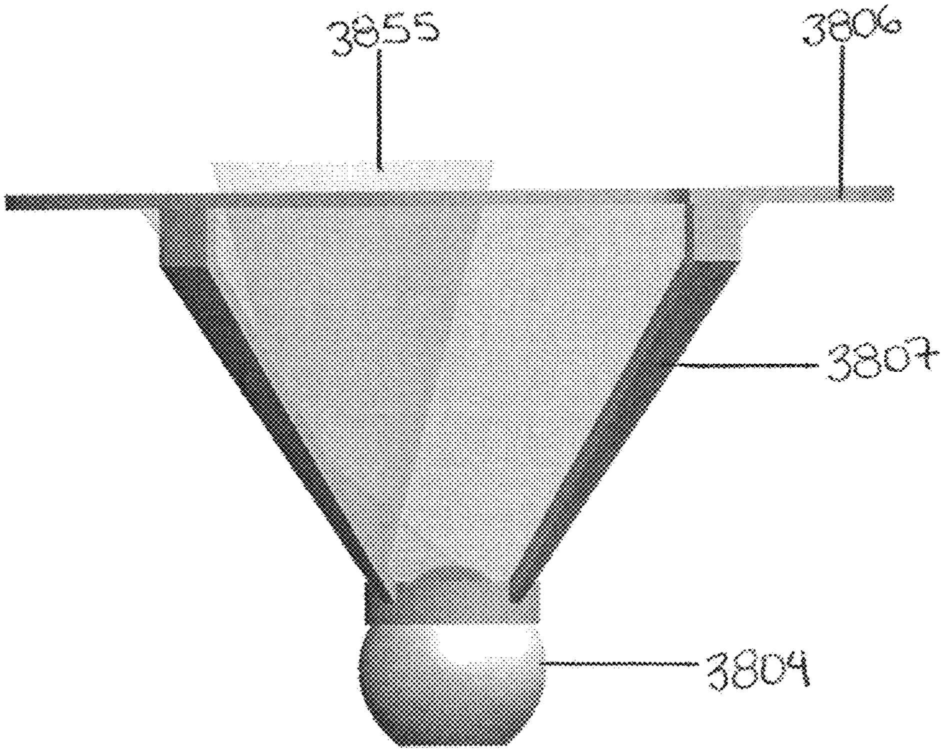
FIG. 40 illustrates a detailed patient interface design
Figure 41:
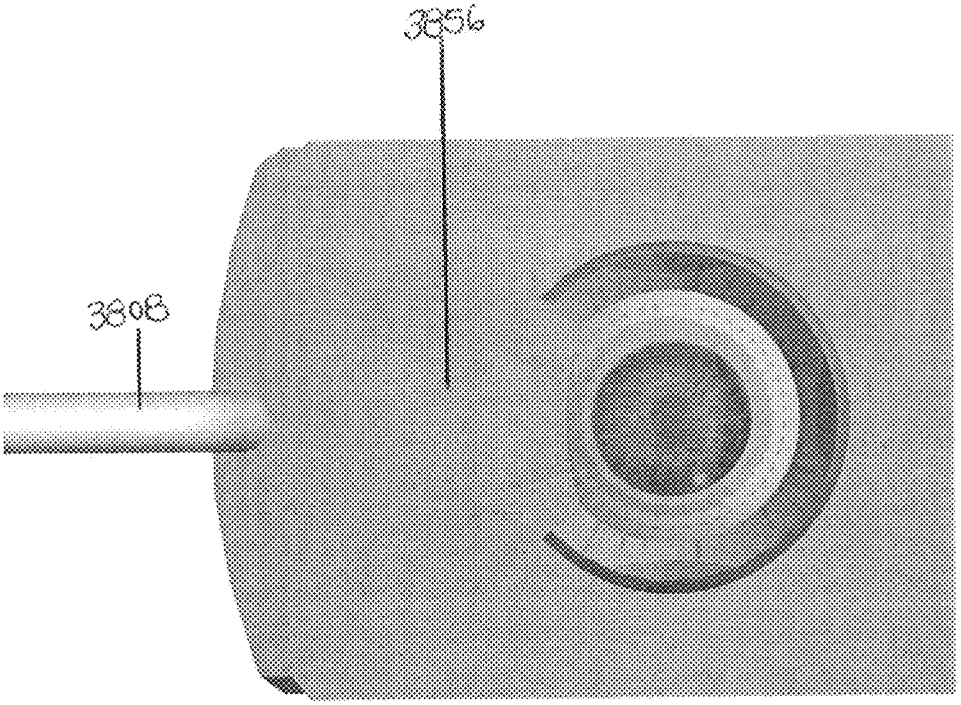
FIG. 41 illustrates a detailed patient interface design
Figure 42:
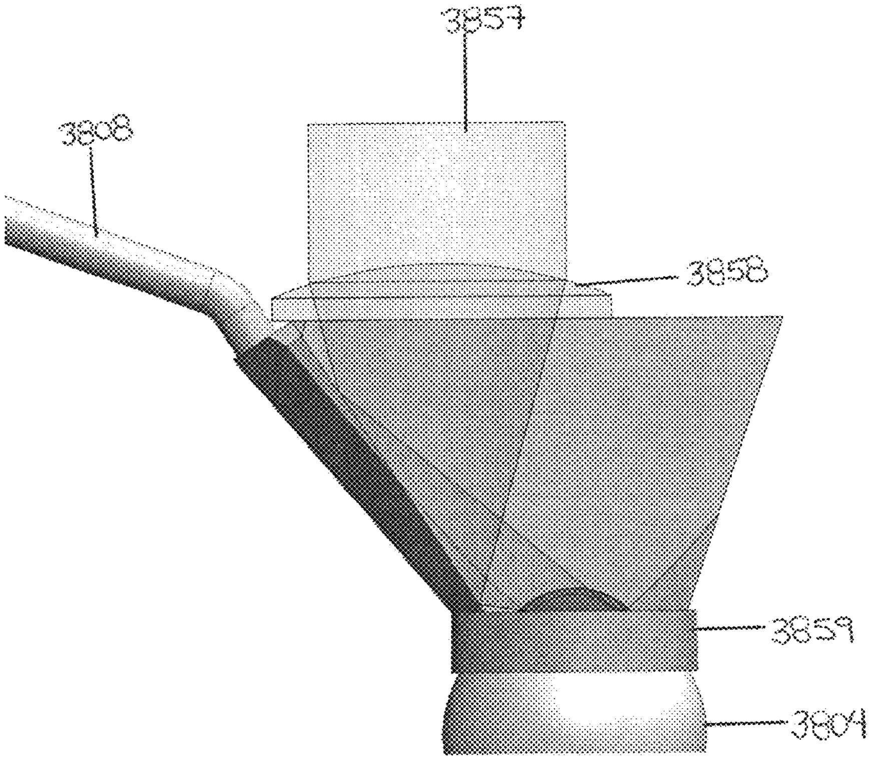
FIG. 42 illustrates a detailed patient interface design
Figure 43:
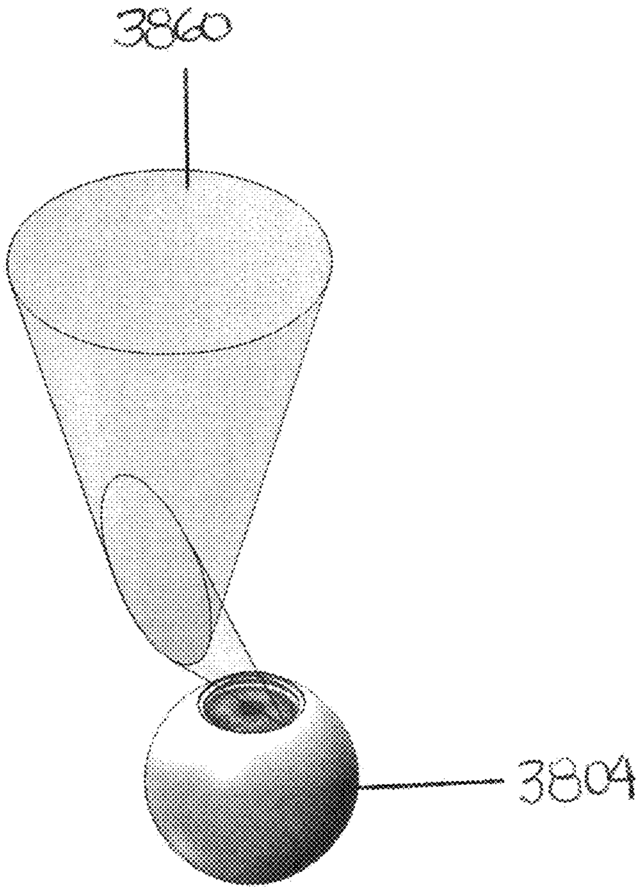
FIG. 43 illustrates a detailed patient interface design
Figure 44:
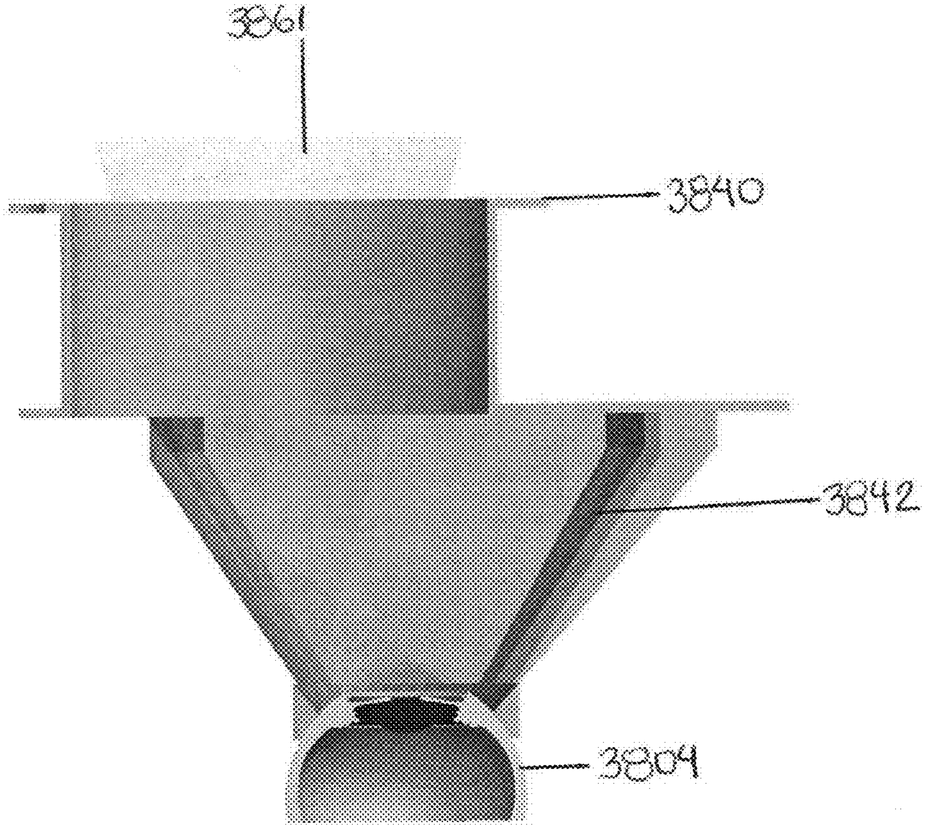
FIG. 44 illustrates a detailed patient interface design
Figure 45:
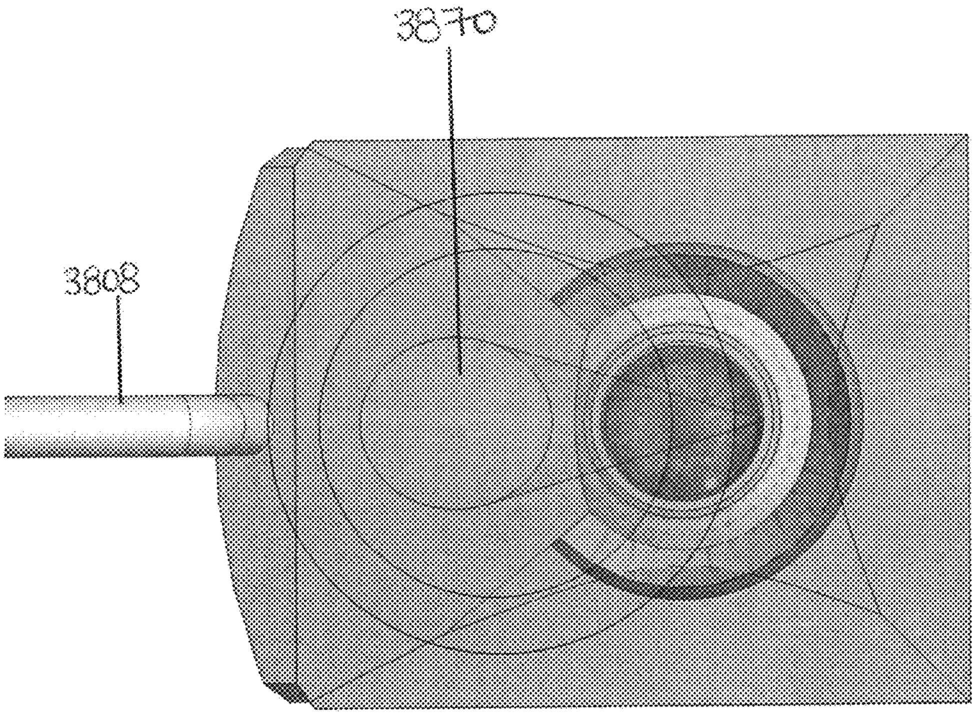
FIG. 45 illustrates a detailed patient interface design
Figure 46:
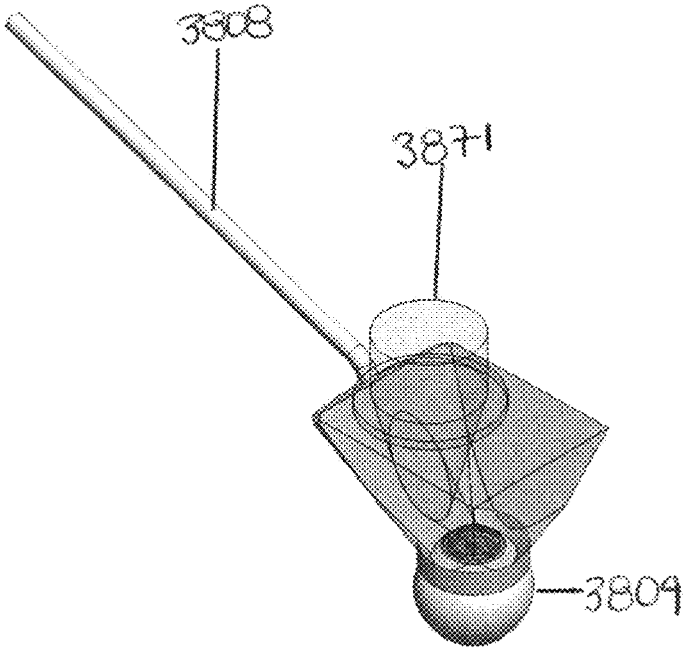
FIG. 46 illustrates a detailed patient interface design
Figure 47:
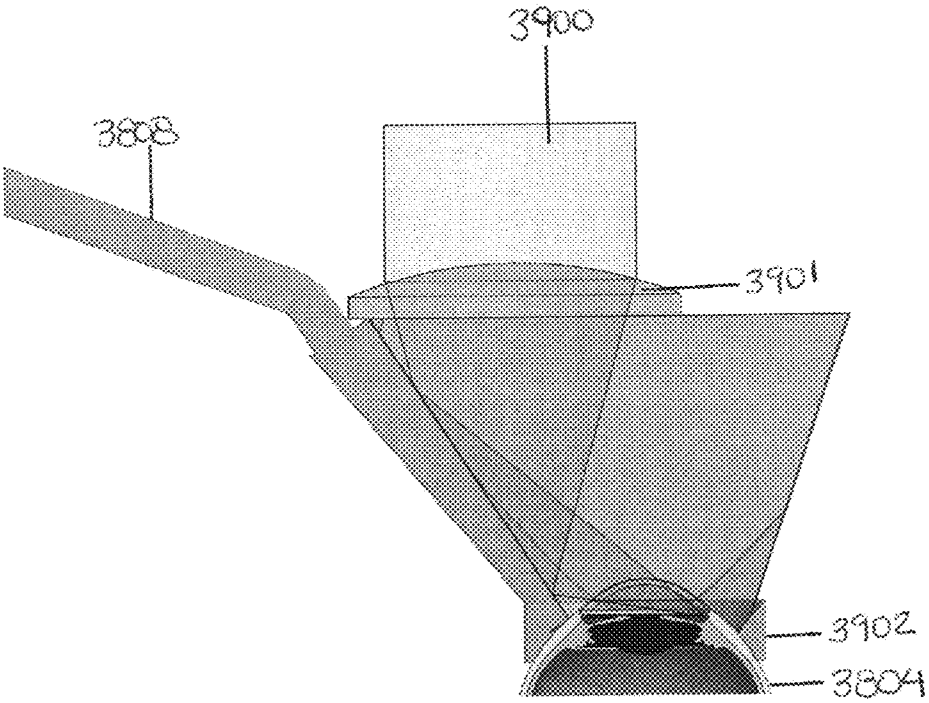
FIG. 47 illustrates a detailed patient interface design

FIG. 38 shows a cross-section of a specific interface that incorporates single large mirror 3950, a scleral flange 3843 and optional suction channel 3814. It allows a laser convergence access angle of 30 deg 3852. The laser beam in its most centered focusing position relative to the anterior angle enters the lower half of the patient interface vertical with an offset to the central line of the eye just like the patient interface in the fourth system above. However this design incorporates a secondary mounting feature on the upper half that is offset such that the laser beam now enters the top of the patient interface centrally. This makes the integration and adaptation to a delivery system above easier since most delivery systems have a preferred central axis laser beam exit. This design includes a mounting ring on top see FIG. 36 that incorporates indexing, reference and locking features 3841 to be connected to a delivery system. This patient interface is used to connect to a surgical delivery system of a photodisruptive laser system. It can also be adapted to an existing medical laser system such as used for femtosecond LASIK or femtosecond laser assisted cataract surgery. FIGS. 36 and 44 show different cross-sections and views of the same patent interface design.

Additional features that apply to some or all of the systems above (first to fifth).

Figure 31:
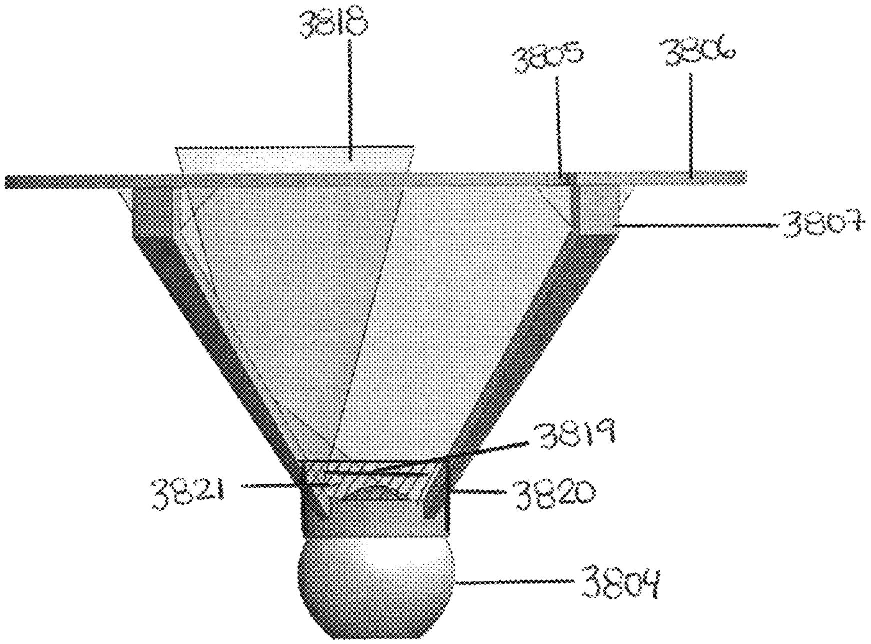
FIG. 31 illustrates a detailed patient interface design
Figure 32:
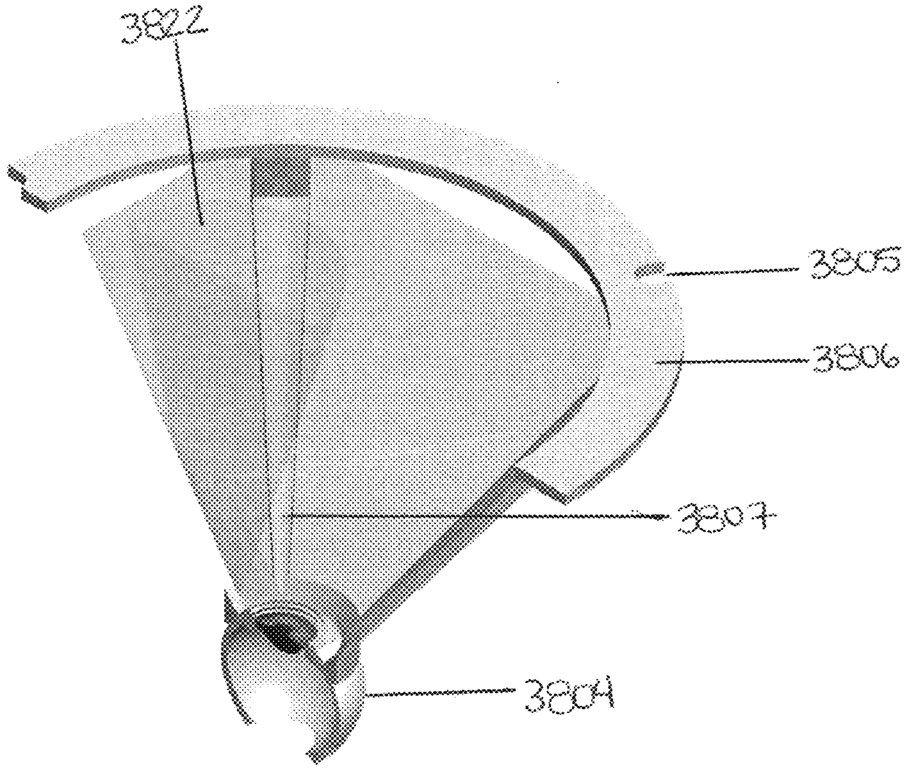
FIG. 32 illustrates a detailed patient interface design

In another implementation see e.g. FIG. 31 all above custom gonio lens and patient interface designs have an upwards extended scleral flange ring 3820 so that its upper rim is at least 1 mm above the highest (central) cornea point. Prior to the procedure a liquid 3821 such as saline or water is filled into the watertight flange volume and therefore the liquid will replace the gonio lens material. The patient is in this version laying on its back, so that gravity keeps the liquid in place. To stabilize any liquid waves a top flat glass piece 3819 is in another implementation placed on the top in contact with the water. This implementation allows more patient comfort and less pressure rise (IOP) during the procedure. FIG. 31 shows this implementation on the patient interface of the forth system above but it is also considered implemented on the design of the first, second, third and fifth system.

In another implementation the first, second, third, fourth and fifth system all are made for handheld operation to be used manually at the slit lamp or under the OR microscope as well.

In another implementation the first, second, third, fourth and fifth system are all made disposable.

A sixth system being a specific low complexity delivery system that allows delivery of photodisruptive laser pulses into the angle region of the anterior chamber of an eye.

The delivery system pieces closest to the eye are mounted in a configuration as shown in FIG. 16. The laser scanning pattern described in the third method above require only small scanning angles of the laser beam originating from a final focusing lens (e.g. FIG. 16). The focusing lens will be >2 cm away from the focus point of the laser. Therefore the delivery system scanning angles through the final focusing lens are limited <5 deg from the main optical axis. This feature allows the use of a simple low complexity focusing lens assembly (e.g. a single aspherical lens). Furthermore a single preferably gimbal mounted scanning mirror above the mirror 3399 in FIG. 16 in combination with a z-scannable lens along the laser beam (e.g. the focusing lens 3402 FIG. 16) is used to perform all scanning patterns as described in the third method.

Figure 18:
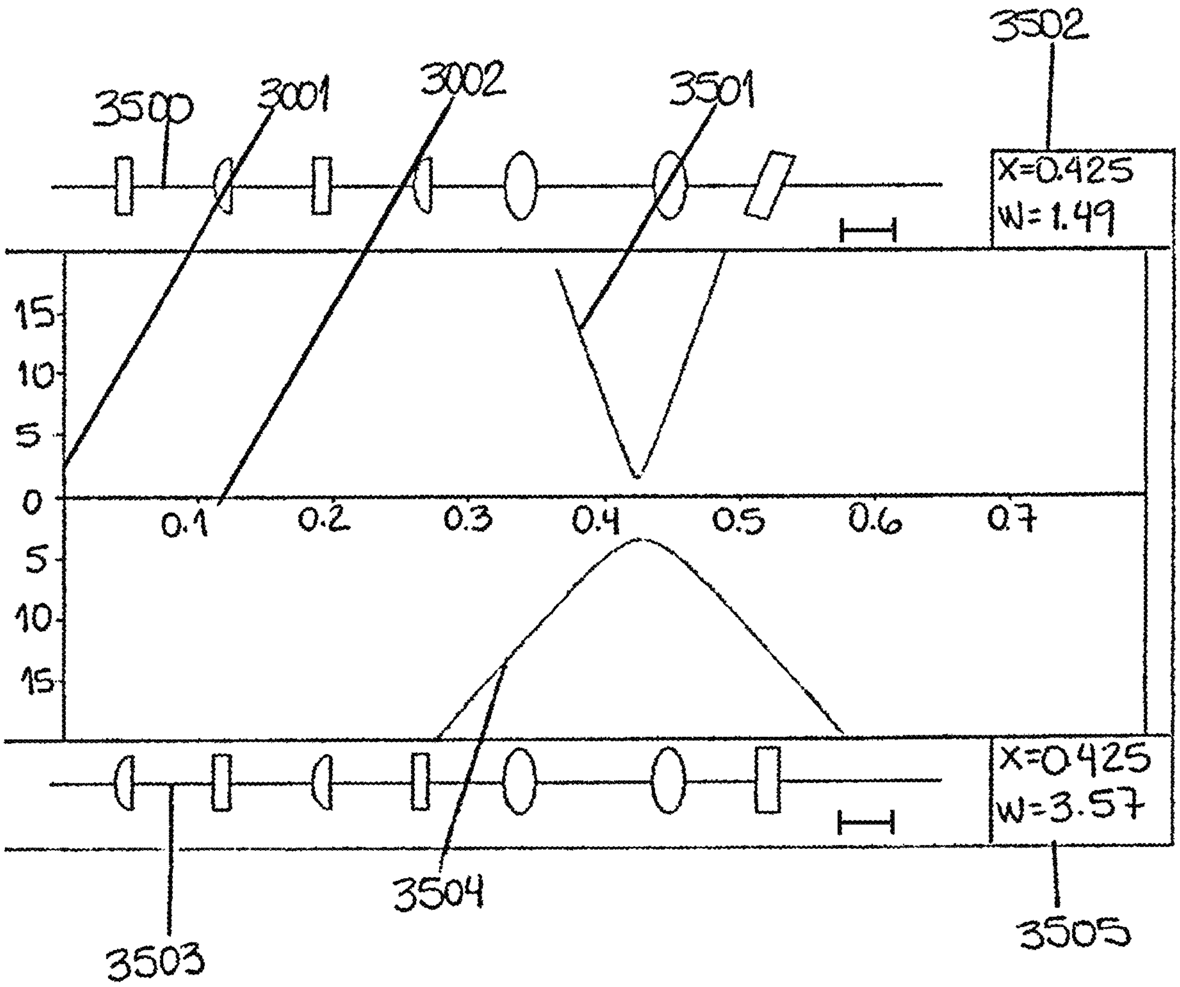
FIG. 18 shows a detailed laser shaping optical delivery system component design
Figure 19:
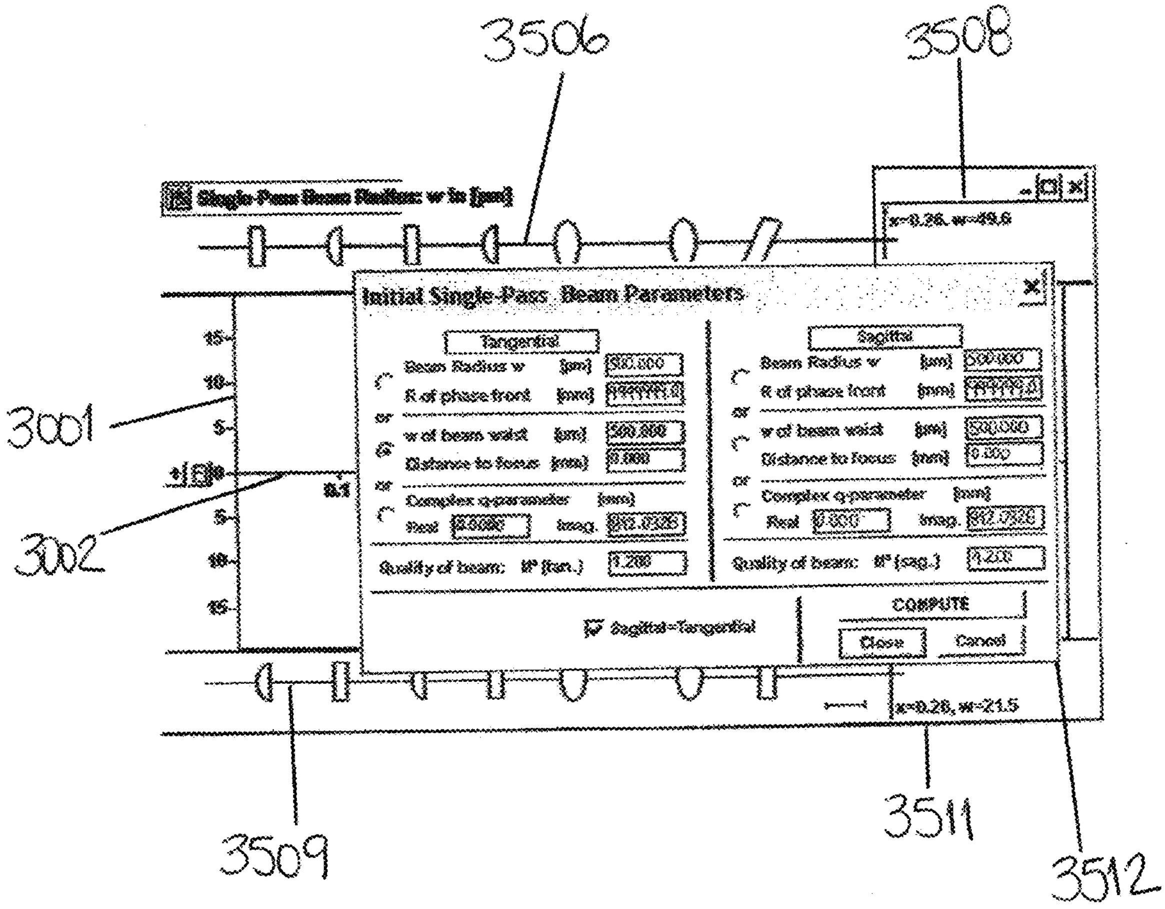
FIG. 19 shows a detailed laser shaping optical delivery system component design
Figure 20:
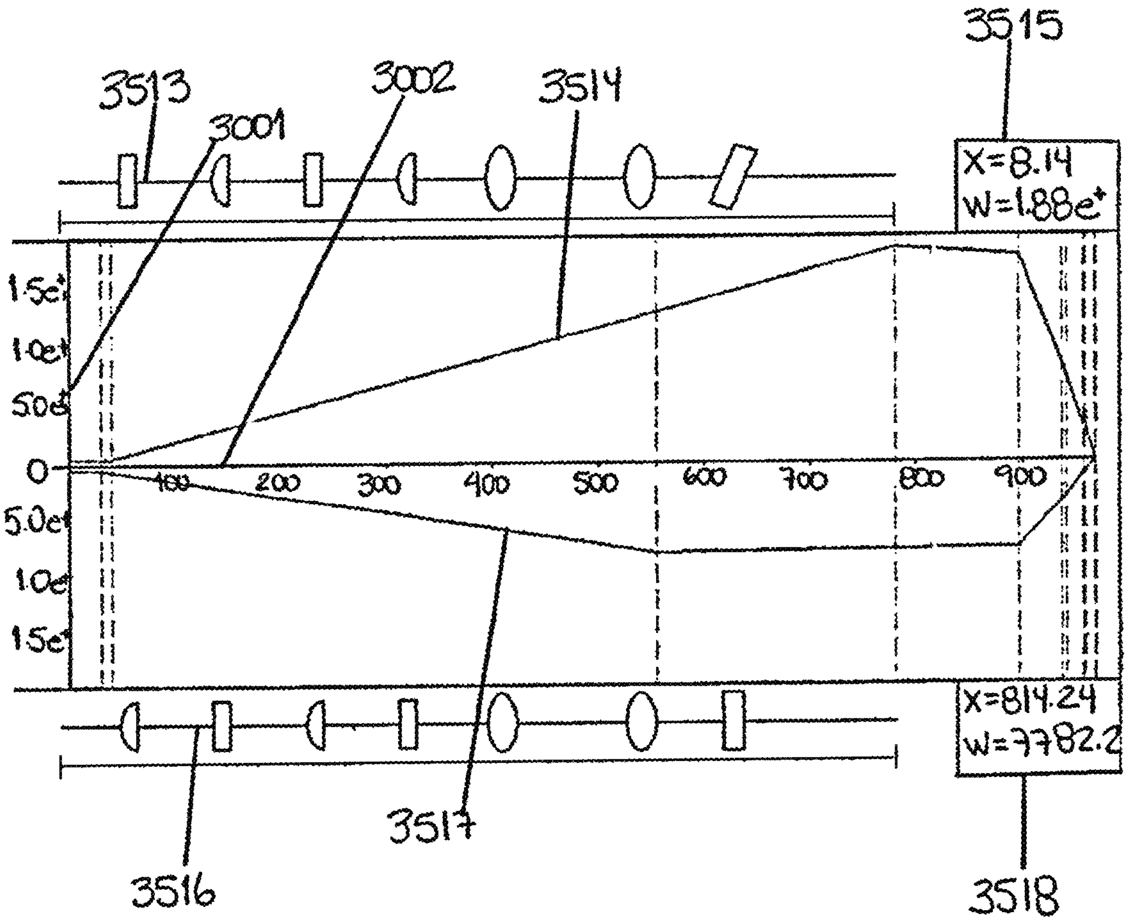
FIG. 20 shows a detailed laser shaping optical delivery system component design
Figure 21:
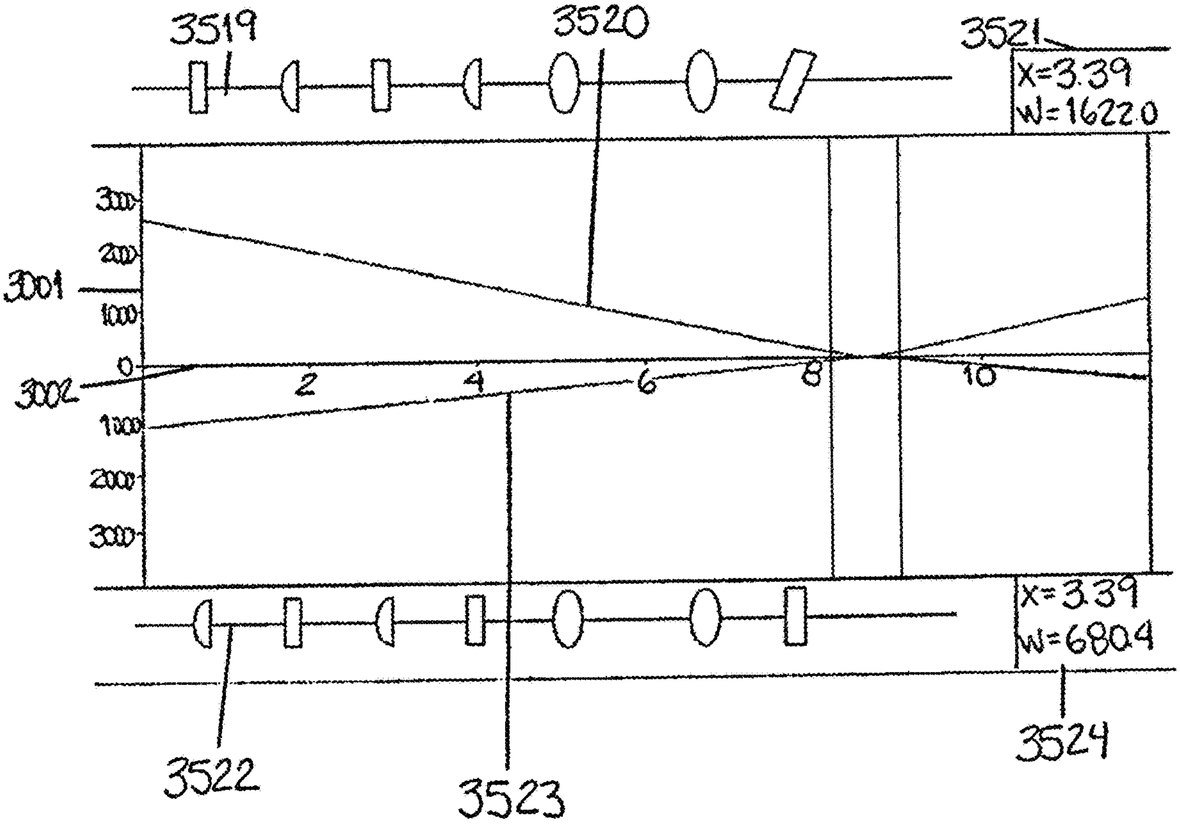
FIG. 21 shows a detailed laser shaping optical delivery system component design

The preferred beam shaping of the described delivery system along the optical beam path is shown in FIGS. 18, 19, 20 and 21. In FIG. 18, 3001 is the y-axis of the graph representing the beam radius in micro meters. 3002 is the x-axis along the beam propagation in mm. 3502 and 3505 show the focus beam radius in the horizontal and respectively vertical axis as well as the focus position in the x-axis. This calculated laser beam propagation graphs show a detailed lens design to achieve laser beam shaping for an elliptical fs-laser spot size onto the Trabecular Meshwork with approximately 3 μm spot size in the horizontal plane and approximately 7 μm spot size in the vertical plane.

Figure 22:
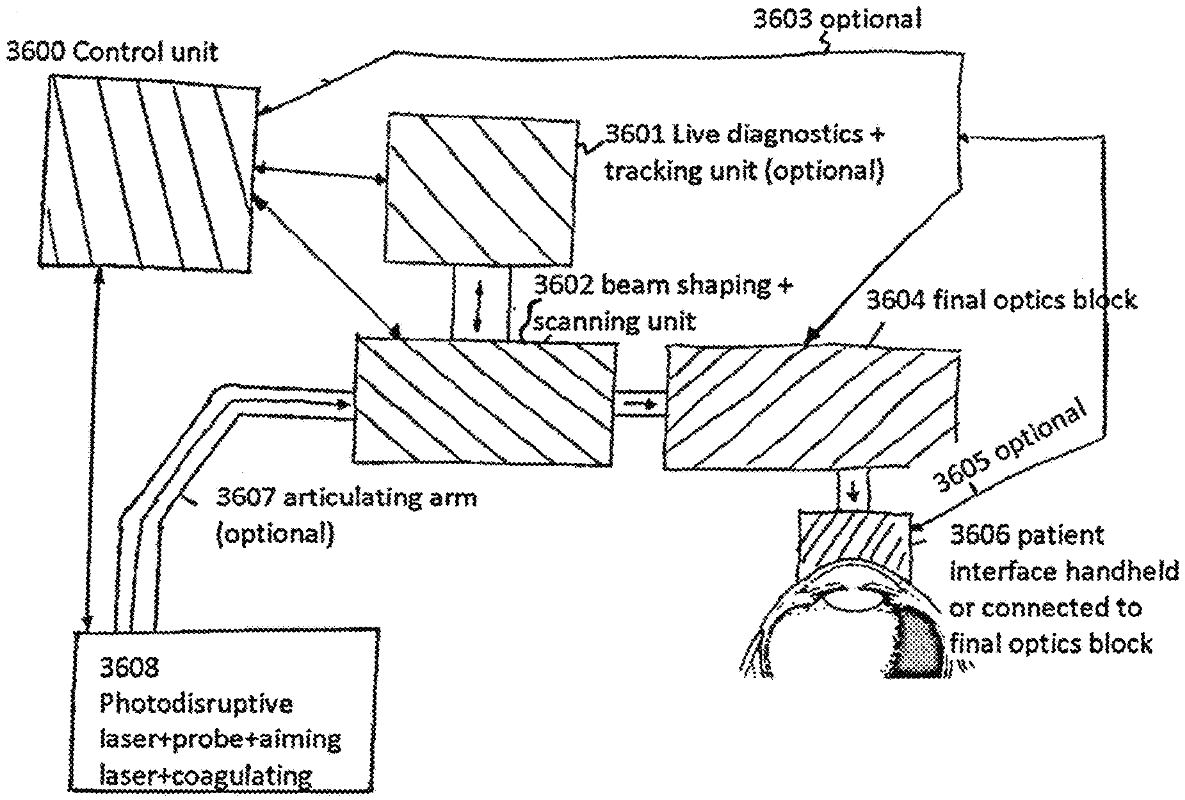
FIG. 22 illustrates a full system block diagram

FIG. 22. Shows a basic system block diagram, of the entire system including the various laser engines 3608, the delivery system (made out of several units) the control unit 3600 the diagnostic and tracking unit 3601, the beam shaping and scanning unit 3602, the final optics block unit 3604 and the patient interface unit 3606. This system applies to several configurations and shows the components and elements of the herein described femtosecond-laser, delivery system and patient interfaces.

In another implementation this delivery system is integrated into a standard surgical microscope.

In another implementation, this delivery system is integrated into a standard slit lamp.

In another implementation, the delivery system is a fs-laser source and custom delivery system as a stand-alone operating room unit.

It should be appreciated that although several different embodiments are shown, any of the features of one embodiment may be used on any of the other embodiments described.

Although the present invention has been described in considerable detail with reference to the preferred versions thereof, other versions are possible.

The scope of the appended claims is limited to only some of the invented details here and is therefore not to be considered complete.

The invention claimed is:

1. A system for treating a target volume of ocular tissue of an anterior angle of an eye with a laser, the target volume of ocular tissue characterized by a distal extent, a proximal extent, and a lateral extent, the system comprising:

a first optical subsystem including a focusing objective configured to be coupled to the eye;

a second optical subsystem including a laser source configured to output a laser beam, and a plurality of components configured to one or more of focus, scan, and direct the laser through the focusing objective, in a direction of propagation toward the target volume of ocular tissue; and a control system coupled to the second optical subsystem and configured to control the focus and scan of the laser to:

initially photodisrupt tissue at an initial depth corresponding to the distal extent of the target volume of ocular tissue; and subsequently photodisrupt tissue at one or more subsequent depths between the distal extent of the target volume of ocular tissue and the proximal extent of the target volume of ocular tissue by scanning a focus of the laser from the initial depth in a direction from the distal extent toward the proximal extent, the direction being opposite the direction of propagation of the laser.

2. The system of claim 1, wherein the control system is configured to control the focus and scan of the laser to repeat the photodisrupting at a plurality of different subsequent depths until tissue at the proximal extent of the target volume of ocular tissue is photodisrupted.

3. The system of claim 1, wherein the control system is further configured to control the focus and scan of the laser to photodisrupt tissue debris or bubbles between the proximal extent of the target volume of ocular tissue and the distal extent of the target volume of ocular tissue by moving the focus of the laser beam in the direction of propagation of the laser beam, after photodisrupting the target volume of ocular tissue.

4. The system of claim 1, wherein the control system controls the focus and scan of the laser during initial or subsequent photodisrupting of tissue by being further configured to:

focus light from a femtosecond laser at a spot in the tissue at the initial depth or at the one or more subsequent depths; and apply optical energy to the tissue.

5. The system of claim 4, wherein the control system controls the focus and scan of the laser during application of optical energy by being further configured to: scan the focus of the laser in multiple directions defining a treatment plane, to thereby photodisrupt an initial layer of tissue of the target volume of ocular tissue or one or more subsequent layers of tissue of the target volume of ocular tissue.

6. The system of claim 1, wherein the control system is further configured to control the focus and scan of the laser to repeat the initial photodisrupting of tissue and the subsequent photodisrupting oft issue one or more times.

7. The system of claim 6, wherein the laser beam has a pulse duration of less than 50,000 femtoseconds.

8. The system of claim 1, further comprising a diagnostic apparatus configured to capture images of ocular tissue, wherein the control system is coupled to the diagnostic apparatus and is configured to detect the target volume extend of ocular tissue.

9. The system of claim 8, wherein the diagnostic apparatus comprises at least one of an optical imaging apparatus, a vision system or an optical coherence tomography system.

10. The system of claim 1, wherein the first optical subsystem comprises a gonio lens.

11. The system of claim 1, wherein the laser beam has a pulse duration of less than 50,000 femtoseconds.

12. The system of claim 1, wherein the plurality of components of the second optical subsystem are configured to scan the laser beam in a circular pattern.

13. A system for treating an eye comprising an anterior chamber, a Schlemm's canal, and a trabecular meshwork therebetween, the system comprising:

a first optical subsystem including a focusing objective configured to be coupled to the eye;

a second optical subsystem including a laser source configured to output a laser beam, and a plurality of components configured to one or more of focus, scan, and direct the laser beam through the focusing objective, toward ocular tissue; and a control system coupled to the second optical subsystem and configured to control the focus and the scan of the laser beam to:

initially photodisrupt ocular tissue at or near an interface between the Schlemm's canal and the trabecular meshwork; and subsequently photodisrupt ocular tissue of the trabecular meshwork.

14. The system of claim 13, wherein the control system controls the focus and scan of the laser beam during initial photodisrupting of ocular tissue by being further configured to:

focus light from a femtosecond laser at a spot in tissue at or near the interface between the Schlemm's canal and the trabecular meshwork; and apply optical energy to the tissue.

15. The system of claim 13, wherein the control system controls the focus and scan of the laser beam during subsequent photodisrupting of ocular tissue by being further configured to: focus light from a femtosecond laser at a spot in tissue of the trabecular meshwork; and apply optical energy to the tissue.

16. The system of claim 13, wherein the control system is further configured to control the focus and scan of the laser beam to repeat the initial photodisrupting of ocular tissue and the subsequent photodisrupting of ocular tissue one or more times until an opening is formed between the anterior chamber and the Schlemm's canal.

17. The system of claim 13, further comprising a diagnostic apparatus configured to capture images of ocular tissue, wherein the control system is coupled to the diagnostic apparatus and is configured to one or more of: detect ocular tissue at or near the trabecular meshwork and the Schlemm's canal; determine a lateral extent of ocular tissue to be photodisrupted.

18. The system of claim 17, wherein the diagnostic apparatus comprises at least one of an optical imaging apparatus, a vision system or an optical coherence tomography system.

19. The system of claim 13, wherein the first optical subsystem comprises a gonio lens.

20. A system for treating a target volume of ocular tissue of an anterior angle of an eye with a laser, the system comprising:

a goniolens configured to be coupled to the eye;

an optical laser subsystem including a laser source configured to output a laser beam and a plurality of components configured to focus, scan, or direct the laser beam through the goniolens toward the target volume of ocular tissue; and a control system in electrical communication with the optical laser subsystem for controlling the focus and scan of the laser beam to (1) initially photodisrupt tissue at an initial depth corresponding to a distal extent of the target volume and (2) to subsequently photodisrupt tissue at a subsequent depth that is proximal to the distal extent of the target volume by scanning a focus of the laser from the distal extent toward the proximal extent of the target volume.

* * * * *